United States Patent
Nolan et al.

(10) Patent No.: US 12,135,300 B2
(45) Date of Patent: *Nov. 5, 2024

(54) SINGLE CELL ANALYSIS USING SECONDARY ION MASS SPECTROMETRY

(71) Applicant: The Board of Trustees of the Leland Stanford Junior University, Stanford, CA (US)

(72) Inventors: Garry P. Nolan, Redwood City, CA (US); Sean C. Bendall, San Mateo, CA (US); Robert M. Angelo, Menlo Park, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 207 days.

This patent is subject to a terminal disclaimer.

(21) Appl. No.: 17/064,311

(22) Filed: Oct. 6, 2020

(65) Prior Publication Data

US 2021/0310970 A1    Oct. 7, 2021

Related U.S. Application Data

(63) Continuation of application No. 16/173,897, filed on Oct. 29, 2018, now abandoned, which is a continuation of application No. 15/679,044, filed on Aug. 16, 2017, now Pat. No. 10,114,004, which is a continuation of application No. 15/068,338, filed on Mar. 11, 2016, now Pat. No. 9,766,224.

(60) Provisional application No. 62/138,322, filed on Mar. 25, 2015.

(51) Int. Cl.
| | |
|---|---|
| *G01N 33/483* | (2006.01) |
| *G01N 23/2258* | (2018.01) |
| *G01N 33/50* | (2006.01) |
| *G01N 33/68* | (2006.01) |
| *H01J 49/00* | (2006.01) |
| *H01J 49/14* | (2006.01) |

(52) U.S. Cl.
CPC ..... *G01N 23/2258* (2013.01); *G01N 33/4833* (2013.01); *G01N 33/5005* (2013.01); *G01N 33/5008* (2013.01); *G01N 33/6848* (2013.01); *H01J 49/0036* (2013.01); *H01J 49/14* (2013.01); *G01N 2458/15* (2013.01); *H01J 49/142* (2013.01)

(58) Field of Classification Search
None
See application file for complete search history.

(56) References Cited

U.S. PATENT DOCUMENTS

| | | |
|---|---|---|
| 6,627,877 B1 | 9/2003 | Davis et al. |
| 6,849,848 B2 | 2/2005 | Baranov et al. |
| 7,700,295 B2 | 4/2010 | Baranov et al. |
| 7,728,287 B2 | 6/2010 | Felton et al. |
| 9,766,224 B2 * | 9/2017 | Nolan ................ G01N 33/5008 |
| 2004/0009962 A1 | 1/2004 | Dickler |
| 2007/0178607 A1 | 8/2007 | Prober et al. |
| 2008/0113875 A1 | 5/2008 | Chaurand et al. |
| 2010/0144056 A1 | 6/2010 | Winnik et al. |
| 2010/0255602 A1 | 10/2010 | Felton et al. |
| 2011/0212850 A1 | 9/2011 | Brodie et al. |
| 2012/0077714 A1 | 3/2012 | Nolan et al. |
| 2012/0172249 A1 | 7/2012 | Ripoll et al. |
| 2013/0122516 A1 | 5/2013 | Hong et al. |
| 2014/0221241 A1 | 8/2014 | Nolan et al. |
| 2014/0329274 A1 | 11/2014 | Bowen et al. |
| 2015/0080233 A1 | 3/2015 | Bendall et al. |

FOREIGN PATENT DOCUMENTS

| | | |
|---|---|---|
| WO | WO 00/68434 A2 | 11/2000 |
| WO | WO 2009/113044 A2 | 9/2009 |
| WO | WO 2009/156725 A1 | 12/2009 |
| WO | WO 2010/116961 A1 | 10/2010 |
| WO | WO 2012/003478 A2 | 1/2012 |
| WO | WO 2014/079802 A2 | 5/2014 |
| WO | WO 2014/169394 A1 | 10/2014 |
| WO | WO 2015/038784 A1 | 3/2015 |
| WO | WO 2015/128490 A1 | 9/2015 |
| WO | WO 2015/153464 A1 | 10/2015 |

OTHER PUBLICATIONS

Barnes et al., "Identifying Individual Cell Types in Heterogeneous A Cultures Using Secondary Ion Mass Spectrometry Imaging with C 60 Etching and Multivariate Analysis". Analytical Chemistry. 2012; 84(2): 893-900.

Geisen et al., "Highly multiplexed imaging of tumor tissues with subcellular resolution by mass cytometry", Nature Methods. 2014; 11(4): 417-22.

McMahon et al., "Quantitative imaging of cells with multi-isotope imaging of mass spectrometry (MIMS)—Nanoautography with stable isotope tracers". Applied Surface Science. 2006; 252(19): 6895-6906.

(Continued)

*Primary Examiner* — Christopher M Gross
(74) *Attorney, Agent, or Firm* — James S. Keddie; Bozicevic, Field & Francis LLP

(57) ABSTRACT

A method of analyzing a population of cells is disclosed. In certain embodiments, the method includes i) obtaining an array of cells on a substrate, wherein the cells are labeled with one or more mass tags and are separated from one another, ii) measuring, using secondary ion mass spectrometry (SIMS), the abundance of the one or more mass tags at a plurality of locations occupied by the cells, thereby generating, for each individual cell measured, a set of data, and iii) outputting the set of data for each of the cells analyzed. Also provided herein are systems that find use in performing the subject method. In some embodiments, the system is an automated system for analyzing a population of cells using SIMS.

19 Claims, 5 Drawing Sheets

(56) References Cited

OTHER PUBLICATIONS

Volandri et al., "An image formation model for Secondary Ion Mass Spectrometry imaging of biological tissue samples". Applied Surface Science. 2010; 257(4): 1267-1275.

Guerquin-Kern et al., "Progress in analytical imaging of the cell by dynamic secondary ion mass spectrometry (SIMS microscopy)", Biochimica et Biophysica Acta, 2005, 1724(3): 228-238.

* cited by examiner

SINGLE CELL ANALYSIS USING SECONDARY ION MASS SPECTROMETRY

CROSS-REFERENCE TO RELATED APPLICATIONS

Pursuant to 35 U.S.C. § 119(e), this application is a continuation of U.S. patent application Ser. No. 16/173,897, filed Oct. 29, 2018, which is a continuation of U.S. patent application Ser. No. 15/679,044, filed Aug. 16, 2017, now issued as U.S. Pat. No. 10,114,004, which is a continuation of U.S. patent application Ser. No. 15/068,338, filed Mar. 11, 2016, now issued as U.S. Pat. No. 9,766,224, which claims the benefit of U.S. Provisional Patent Application No. 62/138,322, filed Mar. 25, 2015, which applications are incorporated herein by reference in their entireties.

GOVERNMENT RIGHTS

This invention was made with Government support under contract W81XWH-12-1-0591 awarded by the Department of Defense and under contracts GM104148 and HHSN268201000034C awarded by the National Institutes of Health. The Government has certain rights in the invention.

BACKGROUND

Cell-based methods for the detection of biomarkers in biological samples, such as blood samples, are important for many applications, including medical diagnostics, disease monitoring and prognosis, and drug discovery. With the current growth and future potential of personalized medicine, there is an increasing demand for rapid, high-throughput and sensitive methods to detect a large number of disease- and individual-specific biomarkers in order to provide personalized diagnoses and therapies to patients. However, most cell-based methods are limited in their multiplexing capabilities, speed, resolution and/or sensitivity.

Flow cytometry, such as fluorescence-activated cell sorting (FACS), is a well-known method for classifying cells and detecting biomarkers based on optical properties of labeled cells. However, conventional flow cytometry is limited in the number of labels that can be used simultaneously because of the spectral overlap between different labels. Additionally, these conventional light-based cytometric methods lack the resolution to provide subcellular distribution of biomarkers—a property that could be related to their activation state or function.

As an alternative to detecting optical signals from a sample, methods to detect molecular mass signatures of a sample using mass spectrometry are known. For example, inductively coupled plasma mass spectrometry (ICPMS) has been used to perform single-cell analysis of a sample by spraying single-cell droplets into an inductively coupled argon plasma to vaporize each cell and ionize the atomic constituents (Bendall et al., Science 2011 332:687). However, ICPMS-based methods are limited in speed, sensitivity, recovery of samples, and inherently does not reveal information related to subcellular localization of labeled targets.

SUMMARY

Described herein is a way to analyze a population of cells which, in certain embodiments, involves making an array of mass-tag labeled cells on a substrate, and analyzing the cells on a cell-by-cell basis using secondary ion mass spectrometry (SIMS). Depending on how the method is implemented, the present method may be done with a high level of multiplexing and with single-molecule sensitivity. In addition, the present method may be done in a high throughput way, and the subcellular location of the labels can be determined. Further, the analyzed cells can be recovered for further analysis. None of these potential advantages is achievable by conventional single cell analysis methods.

In certain embodiments, the method may involve: i) obtaining an array of cells on a substrate, wherein the cells are labeled with one or more mass tags and are separated from one another, ii) measuring, using secondary ion mass spectrometry (SIMS), the abundance of the one or more mass tags at a plurality of locations occupied by the cells, thereby generating, for each individual cell measured, a set of data, and iii) outputting the set of data for each of the cells analyzed. The array of cells may be an addressable array, or a random array. In embodiments of the method where the array of cells is a random array, the locations on the substrate occupied by the cells are determined by imaging the substrate prior to the measuring step. In some embodiments, the imaging is by optical imaging, electron imaging or low resolution SIMS.

In any embodiment, the measuring step may include applying a SIMS ion beam with a diameter equal to or greater than half the average diameter of individual cells to measure the abundance of the one or more mass tags on a whole cell basis. In such embodiments, the ion beam may have a diameter in the range of 1 μm to 50 μm.

In any embodiment, the measuring step may include applying a plurality of pulses of a SIMS ion beam at different sites of an individual cell of the array to obtain measurements of the abundance of the one or more mass tags at the different sites. In such embodiments, the ion beam may have a diameter in the range of 10 nm to 1500 nm. In certain embodiments, the method may include measuring the abundance of the one or more mass tags at a plurality of depths as the SIMS ion beam etches through the individual cell.

In any embodiment, the array of cells may be obtained by labeling cells with one or more mass tags, and attaching cells to a substrate, wherein the labeling is done either prior to or after the cells are attached to the substrate. The labeling may be done by administering the mass tag to an animal subject and obtaining labeled cells from the subject.

In any embodiment, the method may include labeling cells with a first mass tag and a second mass tag, wherein the first mass tag localizes to a known subcellular structure of the cell, measuring the abundance of the first and second mass tags at different sites of an individual cell of the array, and determining the subcellular localization of the second mass tag based on the measured abundance of the first and second mass tags.

In any embodiment, the method may further include identifying one or more cells of interest based on the obtained set of data, and recovering the identified cells for further analysis. In any embodiment, the method may include remeasuring the abundance of the one or more mass tags at a plurality of locations occupied by the identified cells of interest, using SIMS, thereby generating, for each individual cell remeasured, a second set of data, and outputting the second set of data for each of the identified cells of interest.

Also disclosed herein is a method of analyzing a test population of cells. In these embodiments, the method may involve obtaining an array of cells on a substrate, wherein the cells are labeled with one or more mass tags and are separated from one another; measuring, using SIMS, the abundance of the one or more mass tags at a plurality of locations occupied by the cells, thereby generating, for each individual cell measured, a set of data; generating a histogram showing the distribution of the mass tags across the test population of cells; and comparing the histogram to a reference histogram obtained from a reference population of cells.

In any of these embodiments, the method may further include identifying one or more cells of interest based on a threshold value for the abundance of the one or more mass tags. In some cases the threshold value is determined based on the reference histogram.

In any of these embodiments, the test population of cells may have been contacted with a test agent and the reference population of cells has not been contacted with the test agent.

In any of these embodiments, the test population of cells may be obtained from a subject diagnosed with a condition and the reference population of cells is obtained from a healthy subject.

Also provided herein is an automated system for analyzing an array of cells. In certain embodiments, the system may include a SIMS system comprising a holder for retaining a substrate comprising an array of cells, wherein the cells are labeled with one or more mass tags and are separated from one another, wherein the system is configured to (i) measure the abundance of the one or more mass tags at a plurality of locations occupied by the cells of the array using SIMS, (ii) generate a data set that comprises the measurements of the abundance of the one or more mass tags, and (iii) output the data set, and a computer comprising an analysis module that analyzes the data set.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
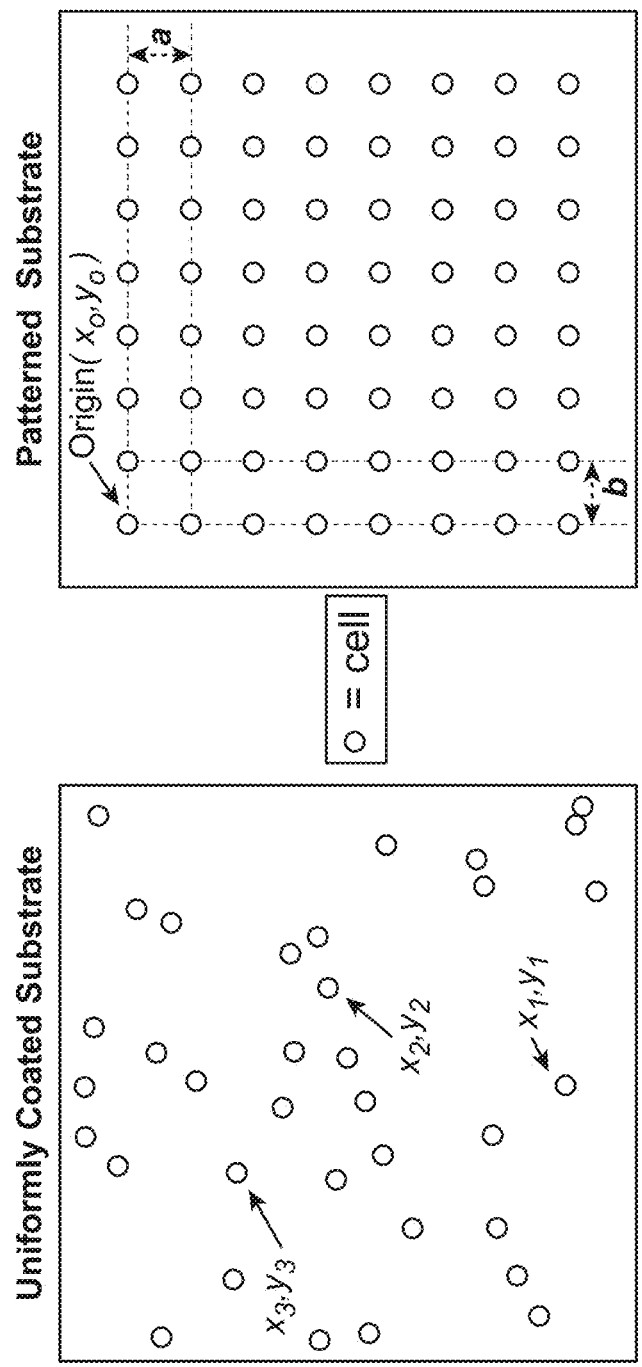
FIG. 1 shows schematic representations of a random (left) and addressable (right) array of cells on a substrate, according to embodiments of the present disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

"Binding," as used herein, refers to a specific interaction between any two members, e.g., two proteins, two nucleic acids, a protein and a nucleic acid, etc., where the affinity between a two specific binding members is characterized by a $K_D$ (dissociation constant) of $10^{-5}$ M or less, $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, including $10^{-16}$ M or less. "Affinity" refers to the strength of binding, increased binding affinity being correlated with a lower $K_D$.

The term "specific binding" refers to the ability of a binding reagent to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

As used herein, the term "specific binding reagent" refers to a labeled reagent that can specifically bind to one or more sites in a specific molecular target (e.g., a specific protein, phospholipid, DNA molecule, or RNA molecule) in or on a cell. Specific binding reagents include antibodies, nucleic acids, and aptamers, for example. A used herein, an "aptamer" is a synthetic oligonucleotide or peptide molecule that specifically binds to a specific target molecule.

By "antibody" is meant a protein of one or more polypeptides that specifically binds an antigen and that are substantially encoded by all or part of the recognized immunoglobulin genes. The recognized immunoglobulin genes, for example in humans, include the kappa (κ), lambda (λ), and heavy chain genetic loci, which together contain the myriad variable region genes, and the constant region genes mu (μ), delta (δ), gamma (γ), sigma (σ), and alpha (α) which encode the IgM, IgD, IgG, IgE, and IgA antibody "isotypes" or "classes" respectively. Antibody herein is meant to include full length antibodies and antibody fragments, and may refer to a natural antibody from any organism, an engineered antibody, or an antibody generated recombinantly for experimental, therapeutic, or other purposes. The term "antibody" includes full length antibodies, and antibody fragments, as are known in the art, such as Fab, Fab', F(ab')2, Fv, scFv, or other antigen-binding subsequences of antibodies, either produced by the modification of whole antibodies or those synthesized de novo using recombinant DNA technologies. Methods for generating antibodies that bind specifically to a target protein or antigen of interest are known. See, e.g., Greenfield, infra.

The terms "polynucleotide", "nucleotide", "nucleotide sequence", "nucleic acid", "nucleic acid molecule", "nucleic acid sequence" and "oligonucleotide" are used interchangeably, and can also include plurals of each respectively depending on the context in which the terms are utilized. They refer to a polymeric form of nucleotides of any length, either deoxyribonucleotides (DNA) or ribonucleotides (RNA), or analogs thereof. Polynucleotides may have any three-dimensional structure, and may perform any function. The following are non-limiting examples of polynucleotides: coding or non-coding regions of a gene or gene fragment, loci (locus) defined from linkage analysis, exons, introns, messenger RNA (mRNA), transfer RNA (tRNA), ribosomal RNA, ribozymes, small interfering RNA, (siRNA), microRNA (miRNA), small nuclear RNA (snRNA), cDNA, recombinant polynucleotides, branched polynucleotides, plasmids, vectors, isolated DNA (A, B and Z structures) of any sequence, PNA, locked nucleic acid (LNA), TNA (treose nucleic acid), isolated RNA of any sequence, nucleic acid probes, and primers. LNA, often referred to as inaccessible RNA, is a modified RNA nucleotide. The ribose moiety of an LNA nucleotide is modified with an extra bridge connecting the 2' and 4' carbons. The bridge "locks" the ribose in the 3'-endo structural conformation, which is often found in the A-form of DNA or RNA, which can significantly improve thermal stability.

A "plurality" contains at least 2 members. In certain cases, a plurality may have at least 10, at least 100, at least 1000, at least 10,000, at least 100,000, at least $10^6$, at least $10^7$, at least $10^8$ or at least $10^9$ or more members.

The term "mixture", as used herein, refers to a combination of elements, e.g., cells, that are interspersed and not in any particular order. A mixture is homogeneous and not spatially separated into its different constituents. Examples of mixtures of elements include a number of different cells that are present in the same aqueous solution in a spatially unaddressed manner.

By "subject" is meant a human or non-human animal (e.g., a non-human primate, mouse, rat, etc.). A "patient." as used herein, refers to a subject in need of treatment of therapy or a subject who has been diagnosed with a disease.

The term "blood sample" or grammatical equivalents thereof refer to a sample of whole blood or a sub-population of cells in whole blood. Sub-populations of cells in whole blood include platelets, red blood cells (erythrocytes), platelets and white blood cells (i.e., peripheral blood leukocytes, which are made up of neutrophils, lymphocites, eosinophils, basophils and monocytes). These five types of while blood cells can be further divided into two groups, granulocytes (which are also known as polymorphonuclear leukeocytes and include neutrophils, eosinophils and basophils) and mononuclear leukocytes (which include monocytes and lymphocytes). Lymphocytes can be further divided into T cells, B cells and NK cells. Peripheral blood cells are found in the circulating pool of blood and not sequestered within the lymphatic system, spleen, liver, or bone marrow. If blood is first contacted with an agent and then a sample of the blood is used in an assay, then a portion or all of the contacted blood may be used in the assay.

As used herein, the term "mass tagged" refers to a molecule that is tagged with either a single kind of stable isotope of an element that is identifiable by its unique mass or mass profile or a combination of the same, where the combination of stable isotopes provides an identifier. Combinations of stable isotopes permit channel compression and/or barcoding. Examples of elements that are identifiable by their mass include noble metals and lanthanide, although other elements may be employed. An element may exist as one or more isotopes, and this term also includes isotopes of positively and negatively metals. The terms "mass tagged" and "elementally tagged" may be used interchangeably herein. The term mass tag is intended to refer to tags that are distinguishable by elemental analysis. Multi-atom moieties that are distinguishable because they have different masses (e.g., peptide tags or the like) are not mass tags because they are not distinguishable by elemental analysis.

As used herein, the term "mass tag" means any isotope of any element, including transition metals, post transition metals, halides, noble metal or lanthanide, that is identifiable by its mass, distinguishable from other mass tags, and used to tag a biologically active material or analyte. A mass tag has an atomic mass that is distinguishable from the atomic masses present in the analytical sample and in the particle of interest. The term "monoisotopic" means that a tag contains a single type of metal isotope (although any one tag may contain multiple metal atoms of the same type).

As used herein, the term "lanthanide" means any element having atomic numbers 58 to 71. Lanthanides are also called "rare earth metals".

As used herein, the term "noble metal" means any of several metallic elements, the electrochemical potential of which is much more positive than the potential of the standard hydrogen electrode, therefore, an element that resists oxidation. Examples include palladium, silver, iridium, platinum and gold.

As used herein, the term "elemental analysis" refers to a method by which the presence and/or abundance of elements of a sample are evaluated.

As used herein, the term "multiplexing" refers to using more than one label for the simultaneous or sequential detection and measurement of biologically active material.

The term "array," as used with reference to an array of cells, refers to an arrangement of single cells on a substrate, where the single cells are spatially separated from one another. Each location of an array of cells is generally occupied by a single cell; in cases in which a location on the substrate is occupied by two or more cells that are not separated from one another (e.g., two cells that are stuck together or two cells that are the same location by chance), those locations can be identified and optionally excluded from analysis. A single substrate can in certain cases contain two or more arrays of cells, where the cells in the different array are barcoded (e.g., using a mass tag or other distinguishable label) in a way that they can be distinguished from one another.

An array may be addressable or random, where an "addressable" array is an array whose elements, e.g., cells, are localized on a substrate at locations that are known prior to the cells being disposed on the substrate. Thus, locations on the substrate where cells can be associated with the substrate, e.g., through covalent or non-covalent bonding, in an addressable array are predetermined. A "random" array is an array wherein the elements, e.g., cells, are distributed on the surface of a substrate at positions that are not predetermined. In some cases, the distribution of cells on a random array may be described by Poisson statistics, such that, e.g., the distribution of distances between cells of a random array is approximated by a Poisson distribution.

The term "separated from one another," as used herein, refers to cells that are spatially separated from the closest neighboring cell. The term "separated from one another" specifically excludes tissue sections, e.g., formalin fixed paraffin embedded tissue samples, and monolayers of cells that have been grown on a surface. An array of cells that are separated from one another is made by depositing cells that are separated from one another on a substrate.

The term "structure," as used with reference to a subcellular structure, refers to structures within a cell that can be distinguished from each other based on physical location. Thus, a subcellular structure may include the plasma membrane, cell wall, cytoplasm, nucleus, nuclear membrane, chromosomes, centrosomes, other organelles (endoplasmic reticulum, golgi, mitochondria, chloroplasts, phagosomes, centrioles, lysosomes, vacuoles, nucleolus, etc.), and the like. A subcellular structure may also be a subcellular compartment.

The term "localize" as used herein with reference to, e.g., a mass tag localizing to a subcellular structure of a cell, refers to the spatial proximity of the mass tag to the specific subcellular structure compared to other subcellular structures. In some cases, a specific binding interaction between an antibody or a nucleic acid linked to the mass tag and a binding partner provides for the mass tag to localize to a subcellular structure that contains or is attached, directly or indirectly, to the binding partner of the antibody or nucleic acid.

DETAILED DESCRIPTION

As summarized above, aspects of the present disclosure include a method of analyzing a population of cells, including i) obtaining an array of cells on a substrate, wherein the cells are labeled with one or more mass tags and are separated from one another, ii) measuring, using secondary ion mass spectrometry (SIMS), the abundance of the one or more mass tags at a plurality of locations occupied by the cells, thereby generating, for each individual cell measured, a set of data, and iii) outputting the set of data for each of the cells analyzed. Also provided herein are systems that find use in performing the subject method. In some embodiments, the system is an automated system for analyzing a population of cells using SIMS.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Where a range of values is provided, it is understood that each intervening value, to the tenth of the unit of the lower limit unless the context clearly dictates otherwise, between the upper and lower limit of that range and any other stated or intervening value in that stated range is encompassed within the present disclosure.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

It must be noted that as used herein and in the appended claims, the singular forms "a," "an." and "the" include plural referents unless the context clearly dictates otherwise. It is further noted that the claims can be drafted to exclude any optional element. As such, this statement is intended to serve as antecedent basis for use of such exclusive terminology as "solely." "only" and the like in connection with the recitation of claim elements, or use of a "negative" limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

One with skill in the art will appreciate that the present invention is not limited in its application to the details of construction, the arrangements of components, category selections, weightings, pre-determined signal limits, or the steps set forth in the description or drawings herein. The invention is capable of other embodiments and of being practiced or being carried out in many different ways.

The practice of various embodiments of the present disclosure employs, unless otherwise indicated, conventional techniques of immunology, biochemistry, chemistry, molecular biology, microbiology, cell biology, genomics and recombinant DNA, which are within the skill of the art. See Green and Sambrook, MOLECULAR CLONING: A LABORATORY MANUAL, $4^{th}$ edition (2012); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), ANTIBODIES, A LABORATORY MANUAL SECOND EDITION (Greenfield, ed. (2012)), and CULTURE OF ANIMAL CELLS, $6^{th}$ Edition (R. I. Freshney, ed. (2010)).

Method

Method of Analyzing a Population of Cells

Aspects of present disclosure include a method of analyzing a population of cells, including obtaining an array of cells on a substrate, wherein the cells are labeled with one or more mass tags and are separated from one another. In some embodiments, the cells are immobilized on the substrate by way of, e.g., covalent or non-covalent attachment to form an array of cells, as described in further detail below. In some embodiments, a population of cells is attached to the substrate to form an array of cells.

The population of cells immobilized on the substrate may be any suitable type of cells. In certain embodiments, the population of cells may be obtained from blood (e.g., may peripheral blood mononuclear cells (PBMC) such as lymphocytes, monocytes, macrophages, etc., red blood cells, neutrophils, eosinophils, basophils, etc., or other cells that are circulating in peripheral blood), cells that are grown in culture as a suspension of single cells, and single cell organism. In some cases the population of cells immobilized on the substrate may be made from a tissue sample (particularly of a soft tissue such as, e.g., spleen, liver or brain) or cultured cells (e.g., human embryonic kidney cells, COS cells, HeLa cells, Chinese hamster ovary cells, cancer cell lines; stem cell lines, such as embryonic stem cells and induced pluripotent stem cells, etc.) that have been trypsinized to physically disassociate the cells from one another.

The substrate may be any convenient substrate for providing an array of cells for use in SIMS. In certain embodiments, the substrate is a flat or substantially flat substrate. In some embodiments, the substrate is a conductive substrate. Conductive substrates of interest include, but are not limited to, a transparent conductive oxide (TCO) coated glass or plastic, a conductive polymer coated glass or plastic, or a semiconductor wafer. Exemplary TCOs include indium tin oxide (ITO), fluorine doped tin oxide (FTO), doped zinc oxide, and the like. Exemplary conductive polymers include, but are not limited to, poly(3,4-ethylenedioxythiophene) (PEDOT)/polystyrene sulfonic acid (PSS), poly(thiophene)s (PT), and the like. Exemplary semiconductor wafers may include, but are not limited to, silicon dioxide, gallium arsenide, and the like. In some embodiments, the substrate is a non-conductive substrate that is made conductive by, e.g., sputter coating an insulating substrate with a layer of metal such as Au or Pt. In some instances, an insulating substrate is a glass or plastic substrate. In such instances, the insulating substrate may be sputter coated with a layer of metal after forming an array of cells on the substrate, as described further below.

In certain embodiments, the substrate is treated to reduce the background interference when measuring, as described further below, the abundance of one or mass tags at a plurality of locations occupied by the cells using SIMS. In some instances, the background interference from the substrate is reduced by depleting elements used as reporter tags in the subject method from the elemental composition of the surface of the substrate.

In certain embodiments, the substrate is coated with a functional group that allows for attachment and/or immobilization of cells when a population of cells is contacted with the surface of the substrate. In some embodiments, the substrate may be coated with a binding moiety that interacts with another functional group to form a bond. Bonds may include covalent bonds and non-covalent interactions, such as, but not limited to, ionic bonds, hydrophobic interactions, hydrogen bonds, van der Waals forces (e.g., London dispersion forces), dipole-dipole interactions, and the like. Thus, in some cases, the substrate may be coated with a binding moiety that reacts to form a covalent bond with an appropriate functional group on a cell, an antibody, an oligonucleotide, or other members of a binding pair (e.g., avidin-streptavidin). Covalent bonds between the binding moiety and the functional group include covalent bonds that involve reactive groups, such as, but not limited to, the following: glutaraldehyde, which utilizes the bifunctional linker glutaraldehyde to form covalent bonds with amino/amide groups; glycidyl functional groups (i.e., the epoxy functional group) for covalent bonding; 4-nitrophenyl groups, which can be used to acylate amine groups for covalently bonding; N-hydroxysuccinimidyl (NHS) that interact with amino groups. Specific cell cross-linking attachments and reagents of interest include, but are not limited to, amine-terminated surfaces having a fixative or amine-amine crosslinkers (e.g., paraformaldehyde (PFA), glutaraldehyde, NHS esters, imidoesters); carboxyl-terminated surfaces having carboxyolamine crosslinkers (e.g., N,N'-Dicyclohexylcarbodiimide, 1-ethyl-3-(3-dimethylaminopropyl)carbodiimide); thiol-terminated surfaces having amine-thiol cross linkers (e.g., NHS-haloacetyl compounds, NHS-maleimaide, NHS-pyridyldithiol). In some embodiments, the substrate may be coated with a binding moiety that provides an attachment site for cells to bind non-covalently to the substrate surface. In some instances, the binding moieties include, but are not limited to, oligonucleotides, antibodies, and other members of a binding pair (e.g., avidin-streptavidin).

In certain embodiments, the binding moiety coated on the substrate is configured to provide attachment sites on the substrate such that cells attached to the substrate form an array of cells. The attachment sites for the cells may be configured in any suitable manner, and may be configured to form a random or addressable array of cells (FIG. 1). In some embodiments, the substrate is coated with a binding moiety such that attachment sites for each individual cell are not restricted to specific locations on the substrate. In certain instances, an array of cells formed by contacting a suspension of cells with a substrate having cell attachment sites that are not restricted to specific locations on the substrate is a random array of cells. In such instances, cells of a random array may be distributed across the substrate such that the cells do not form a repeating pattern across the substrate. In some embodiments, the substrate is coated uniformly with a binding moiety such that the likelihood of a cell being attached to any given location on the substrate is substantially the same wherever the binding moiety is present. In some instances, the distribution of cells in a random array of cells may be described by Poisson statistics, such that the distribution of distances between cells of a random array may be approximated by a Poisson distribution. In some embodiments wherein the array of cells on a substrate is a random array of cells, the locations occupied by the cells are determined by imaging methods, as described in further detail below.

In certain instances, an array of cells formed on a substrate having cell attachment sites for each individual cell that are not restricted to specific locations on the substrate is an addressable array of cells. In such instances, an addressable array of cells may be formed by separately depositing and attaching individual cells of the suspension of cells at addressable locations on the substrate.

In some embodiments, the substrate is coated with a binding moiety such that each attachment site for cells is addressable. In other words, the substrate may be pattern-coated with a binding moiety to form a predetermined spatial distribution of attachments sites for the cells. In these instances, the substrate may have cell attachment sites for each individual cell that are restricted to specific locations on the substrate. In such instances, an addressable array of cells may be formed by contacting a suspension of cells with a substrate having addressable attachment sites. Methods of making a substrate for forming an addressable array of cells are described in, e.g., Liu et al., Lab Chip. 2013 13:1316; Li et al., Lab Chip. 2008 8:2105; Ren et al., Sens Actuators B Chem. 2013 188:340, which are incorporated by reference. Commercial sources of substrates for forming an addressable array of cells include, e.g., ALSTEM Single Cell Array Coverslips.

In some embodiments, the substrate is both adherent and conductive to facilitate SIMS analysis. For instance, glass or silica surfaces coated with gold, rhodium, or platinum would bind protein moieties of the cells while maintaining substrate conductivity.

In some instances, an array of cells may be formed on a substrate by contacting the substrate with a suspension of cells wherein the concentration of cells in the suspension has been adjusted appropriately to obtain a desired density of cells on the array. In certain embodiments, the density of cells on the substrate is such that the cells in the array are separated from one another. In some instances, each element of an array of cells on a substrate can be assigned on average to a single cell. Thus in some instances, each element of an array of cells on a substrate has on average a single cell, and the distribution of the number of cells at each element of an array may follow a Poisson distribution with a mean of 1. In some instances a minor fraction of elements of an array of cells on a substrate may contain 2 or more cells, while a major fraction may contain 1 cell. Elements of the array that contain 2 or more cells may be removed from analysis, as described in detail below.

In certain embodiments, the density of cells on the substrate is such that the average distance between a cell and its nearest neighbor, as measured between the edge of each cell closest to the other, is 0.1 cell diameters or more, e.g., 0.2 cell diameters or more, 0.5 cell diameters or more, including 1 cell diameters or more, and may be 10 cell diameters or less, e.g., 9 cell diameters or less, 8 cell diameters or less, 6 cell diameters or less, 5 cell diameters or less, 4 cell diameters or less, or 3 cell diameters or less, wherein a cell diameter is the average diameter of the cells. In certain embodiments, the density of cells on the substrate is such that the average distance between a cell and its nearest neighbor, as measured between the edge of each cell closest to the other, is in the range of 0.1 to 10 cell diameters, e.g., 0.3 to 8 cell diameters, 0.5 to 6 cell diameters, 0.75 to 3.5 cell diameters, including 1 to 3 cell diameters, wherein a cell diameter is the average diameter of the cells. In certain embodiments, the density of cells on the substrate is such that the average distance between a cell and its nearest neighbor, as measured between the edge of each cell closest to the other, is 0.2 µm or more, e.g., 0.3 µm or more, 0.4 µm or more, 0.6 µm or more, 0.8 µm or more, 1 µm or more, including 2 µm or more, and may be 500 µm or less, e.g., 300 µm or less, 150 µm or less, 100 µm or less, 80 µm or less, or 60 µm or less. In certain embodiments, the density of cells on the substrate is such that the average distance between a cell and its nearest neighbor, as measured between the edge of each cell closest to the other, is in the range of 0.2 µm to 500 µm, e.g., 0.4 µm to 200 µm, 0.6 µm to 100 µm, 0.8 µm to 50 µm, 1 µm to 40 µm, including 2 µm to 30 µm.

In certain embodiments, the density of cells on the substrate is adjusted to maximize the average number of cells per unit area of the substrate while remaining separated from one another, as described above. In certain embodiments, the density of cells on the substrate may be 100 cells/mm$^2$ or more, e.g., 500 cells/mm$^2$ or more, 1,000 cells/mm$^2$ or more, 1,500 cells/mm$^2$ or more, 2,000 cells/mm$^2$ or more, 2,500 cells/mm$^2$ or more, 3,000 cells/mm$^2$ or more, 3,500 cells/mm$^2$ or more, 4,000 cells/mm$^2$ or more, including 5,000 cells/mm$^2$ or more, and may be 500,000 cells/mm$^2$ or less, e.g., 250,000 cells/mm$^2$ or less, 100,000 cells/mm$^2$ or less, 50,000 cells/mm$^2$ or less, 20,000 cells/mm$^2$ or less, 10,000 cells/mm$^2$ or less, 8,000 cells/mm$^2$ or less, 6,000 cells/mm$^2$ or less, or 4,000 cells/mm$^2$ or less, while remaining separated from one another. In certain embodiments, the density of cells on the substrate may be in the range of 100 to 500,000 cells/mm$^2$, e.g., 500 to 250,000 cells/mm$^2$, 1,000 to 100,000 cells/mm$^2$, 1,500 to 50,000 cells/mm$^2$, or 2,000 to 10,000 cells/mm$^2$, while remaining separated from one another.

Contacting the substrate with a suspension of cells may be performed using any appropriate method, including spot methods or smear methods. In spot methods, cells in suspension at an appropriate density, as described above, are spotted on the substrate and allowed to settle. In some embodiments, the substrate is coated with a cross-linking binding moiety, and the spotted cells are attached to the substrate by first removing the medium in which the cells are spotted and the substrate surface is coated with a cross linking reagent to cross link the cells to the substrate. In certain embodiments, the substrate is coated with a non-covalently bonding moiety, such as an antibody or oligo-nucleotide, as described above, and the cells attach to the substrate surface upon settling. In smearing methods, cells in suspension at an appropriate density, as described above, are smeared on the substrate and the substrate is allowed to air dry. In certain embodiments, cells on the dried substrate may be contacted with a fixing solvent, such as ethanol or methanol. In some embodiments, a suspension of cells may be contacted with a substrate using a cytospin method. In cytospin methods, a suspension of cells at an appropriate density is disposed on a substrate, e.g., a coated coverslip. The substrate is then spun in a centrifuge, e.g. a cytocentrifuge, allowing the cells to settle onto the substrate.

In some embodiments, the substrate may contain a plurality of arrays of cells, each array being composed of a portion, i.e., a subpopulation, of a population of cells. The different subpopulation of cells may be part of a complex sample of cells, such as a blood sample, that contains many different subpopulations of cells that are distinguishable based on physical or functional properties, such as size, shape, expression of cell-surface markers, etc. In some instances, the subpopulations of cells may be derived from a uniform population of cells in suspension that are divided into a plurality of subpopulations of cells, where the plurality of subpopulation of cells are then labeled with a barcoding label specific to each subpopulation, and the barcoded subpopulations mixed together to generate a sample population of cells containing barcoded subpopulations.

In some embodiments where the substrate contains a plurality of arrays of cells, the cells are separated from one another at least within each subpopulation that makes up an array. Thus, in certain embodiments where the substrate contains a plurality of array of cells, the cells may not be separated from one another for the entire population of cells but the cells are separated from one another at least within each array.

The method described herein employs a mass tag, i.e., a stable isotope that is identifiable by its mass for labeling of a biological sample that contains cells and extracellular structures, measured on an instrument capable of quantifying elemental composition with spatial registration using a secondary ion mass spectrometer, e.g., static or dynamic SIMS.

Mass tags may be any suitable mass tags that may be used to label a cell. The mass tag may be part of or conjugated to a stain, or conjugated to a capture agent such as an antibody. In certain embodiments, mass tags may be composed of a chelating polymer made up of repeating units of a metal chelator, such as ethylenediaminetetraacetic acid (EDTA) or diethylene triamine pentaacetic acid (DTPA), chelated to one or more atoms of a single non-biological isotope. In some embodiments the mass tags may be substantially uniform in size, so the abundance of specific binding reagent will be in direct proportion with the number of tag atoms.

Many elements exist in nature as multiple stable isotopes. For example, $^{153}$Eu accounts for 52% of europium on Earth and $^{151}$Eu makes up most of the remaining 48%, while unstable, radioactive isotopes of europium constitute less than 1%. Many stable isotopes are commercially available as powders or salt preparations, in varying degrees of purity, including 99% (2N), 99.9% (3N), 99.99% (4N), 99.999% (5N) and 99.9999% (6N) pure. In some embodiments, metal chelator tags may be synthesized using enriched isotopes. For example, mass dots may be synthesized using $^{151}$Eu (e.g. Europium 151 Oxide, 99.999% purity, American Elements). Mass dots are described in US patent publication 2012/0178183, which is incorporated herein by reference. Using enriched isotopes maximizes the number of unique species of isotope tags that can be simultaneously detected in a multiplexed analysis. In addition, spatially distinct features of interest may be labeled with the same metal tag to further multiplex the analysis. Such spatially distinct features may be distinguished based on co-localization with one or more other metal tags. For example, a Her2 membrane stain and an ER nuclear stain using the same metal tag may be distinguished from one based on a dsDNA or histone H3 stain that uses a different metal tag, which would co-localize with the ER stain.

The mass tag may be part of or conjugated to a stain. In these embodiments, the stain may be phalloidin, gadodiamide, acridine orange, bismarck brown, barmine, Coomassie blue, bresyl violet, brystal violet, 4',6-diamidino-2-phenylindole (DAPI), hematoxylin, cosin, ethidium bromide, acid fuchsine, haematoxylin, hoechst stains, iodine, malachite green, methyl green, methylene blue, neutral red, Nile blue, Nile red, osmium tetroxide (formal name: osmium tetraoxide), rhodamine, safranin, phosphotungstic acid, osmium tetroxide, ruthenium tetroxide, ammonium molybdate, cadmium iodide, carbohydrazide, ferric chloride, hexamine, indium trichloride, lanthanum nitrate, lead acetate, lead citrate, lead(II) nitrate, periodic acid, phosphomolybdic acid, potassium ferricyanide, potassium ferrocyanide, ruthenium red, silver nitrate, silver proteinate, sodium chloroaurate, thallium nitrate, thiosemicarbazide, uranyl acetate, uranyl nitrate, vanadyl sulfate, or any derivative thereof. The stain may be specific for any feature of interest, such as a protein or class of proteins, phospholipids, DNA (e.g., dsDNA, ssDNA), RNA, an organelle (e.g., cell membrane, mitochondria, endoplasmic recticulum, golgi body, nulear envelope, and so forth), a compartment of the cell (e.g., cytosol, nuclear fraction, and so forth). The stain may enhance contrast or imaging of intracellular or extracellular structures.

In certain embodiments, the stain may be suitable for administration to a live subject. The stain may be administered to the subject by any suitable means, such as ingestion, injection (e.g., into the blood circulation), or topical administration (e.g., during a surgery). Such a stain may be specific for a tissue, biological structure (e.g., blood vessel, lesion), or cell type of interest. The stain may be incorporated into cells of the subject of a cellular process, such as glucose uptake. Examples of such stains include, without limitation, gadolinium, cisplatin, halogenated carbohydrates (e.g., carbohydrates which are fluorinated, chlorinated, brominated, iodinated), and so forth. Other injectable stains used in imaging techniques (e.g., such as magnetic resonance imaging (MRI), positron emission tomography (PET) scans, computerized tomography (CT) scans and so forth) may be conjugated to a mass tag if not inherently associated with a mass tag, and administered to a live subject. A sample may be obtained from the subject after administration, for use in the method described herein.

In other embodiments, and as will be described in greater detail below, the mass tag may be conjugated to a capture agent, e.g., an antibody that recognizes an epitope on the sample. In a multiplexed assay, a combination of capture agents and stains may be used.

The mass tag used in the method may be any stable isotope that is not commonly found in the sample under analysis. These may include, but are not limited to, the high molecular weight members of the transition metals (e.g. Rh, Ir, Cd, Au), post-transition metals (e.g. Al, Ga, In, Tl), metalloids (e.g. Te, Bi), alkaline metals, halogens, and actinides, although others may be used in some circumstances. A mass tag may have a mass in the range of 21 to 238 atomic mass units. In certain embodiments, a lanthanide may be use. The lanthanide series of the periodic table comprises 15 elements, 14 of which have stable isotopes (La, Ce, Pr, Nd, Sm, Eu, Gd, Tb, Dy, Ho, Er, Tm, Yb, Lu). Lanthanindes can be readily used because of their rarity in the biosphere. There are greater than 100, non-biological stable isotopes of elements between 1 and 238 atomic mass units (amu). In some embodiments, tagging isotopes may comprise non-lanthanide elements that can form stable metal chelator tags for the applications described herein. In SIMS-based measurement modality, unlike some inductively coupled plasma mass spectrometry (ICP-MS)-based modalities, the elemental reporter could also consist of lower MW, transition elements not common in biological matrices (e.g. Al, W, and Hg).

Elements suitable for use in this method in certain embodiments include, but are not limited to, lanthanides and noble metals. In certain cases, an elemental tag may have an atomic number of 21-92. In particular embodiments, the elemental tag may contain a transition metal, i.e., an element having the following atomic numbers, 21-29, 39-47, 57-79, and 89. Transition elements include the lanthanides and noble metals. See, e.g., Cotton and Wilkinson, 1972, pages 528-530. The elemental tags employed herein are non-biological in that they are not present in typical biological samples, e.g., cells, unless they are provided exogenously.

In particular embodiments, the mass tag to be linked to the binding reagent may be of the formula: R-MT, where R is a reactive group that can form a linkage with a reactive group on a specific binding reagent and MT is a mass tag. The compound may also contain a spacer between R and MT. In particular embodiments. R may be, e.g., a maleimide or halogen-containing group that is sulhydryl reactive, an N-hydroxysuccinimide (NHS)-carbonate that is amine-reactive or an N,N-diisopropyl-2-cyanoethyl phosphoramidite that is hydroxyl-reactive. Such groups react with other groups on the specific binding reagent, e.g., a cysteine or other residue of an antibody or a sulfhydryl group of an oligonucleotide). In many embodiments, the linkage between the reactive group and the mass tag is not selectively cleavable, e.g., is not photo-cleavable.

In particular embodiments, MT may be a polymer of, e.g., 10-500 units, where each unit of the polymer contains a coordinated transition metal. Suitable reactive groups and polymers containing coordinating groups, including 1,4,7,10-tetraazacyclododecane-1,4,7,10-tetraacetic acid (DOTA) and DTPA-based polychelants, are described in a variety of publications, including: Manabe et al. (Biochemica et Biophysica Acta 883: 460-467 (1986)) who describes attaching up to 105 DTPA residues onto a poly-L-lysine backbone using the cyclic anhydride method and also attaching polylysine-poly-DTPA polychelants onto monoclonal antibody (anti-human leukocyte antigen (HLA) $IgG_1$) using a 2-pyridyl disulphide linker achieving a substitution of up to about 42.5 chelants (DTPA residues) per site-specific macromolecule; Torchilin (U.S. Pat. No. 6,203,775) who describes a generic method for labeling antibodies that includes an antibody-reactive, lanthanide chelating compound of a generic formula; Sieving (U.S. Pat. No. 5,364,614), the abstract for describes a DOTA-based polychelant containing a polylysine backbone that is linked to a protein. Further descriptions of such moieties are described in, for example: US20080003616 (Polymer backbone element tags), U.S. Pat. No. 6,203,775 (Chelating polymers for labeling of proteins), U.S. Pat. No. 7,267,994 (Element-coded affinity tags), U.S. Pat. No. 6,274,713 (Polychelants) and U.S. Pat. No. 5,364,613 (Polychelants containing macrocyclic chelant moieties), as well as many others. These publications are incorporated by references for their generic and specific teachings of reactive groups and polymers containing coordinating groups, as well as the methods that can make such compounds. In addition to the methods described in the references cited above, methods for making polymer-based elemental tags are also described in detail in Zhang et al (Agnew Chem. Int. Ed. Engl. 2007 46: 6111-6114). In addition, any chelator able to bind to metal tags can be used. These include EDTA, ethylene glycol tetraacetic acid (EGTA), and Heme. These chelators are able to bind to +1, +2, +3, +4 ions of metal tags. Methods for linking such tags to binding reagents are known in the art. For example, the MAXPAR reagents produced by Fluidigm Sciences is a maleimide-functionalized polymer of DTPA, with an average length of 30 monomers. Using the MAXPAR protocol, it is possible to conjugate a typical IgG antibody with 4-8 polymers, thereby conjugating an average of 200 tagging isotope atoms per antibody.

When using mass-based elemental analysis there are more than 100 non-biological elemental isotopic masses available between 21 and 238 amu that can be simultaneously measured with virtually no overlap. Because these elements are not usually present in biological isolates, the only limitations of detection are the sensitivity of the reagents to which they are conjugated, and the sensitivity of the instrument performing the measurement.

In particular embodiments, the method described above may be employed in a multiplex assay in which a heterogeneous population of cells is labeled with a plurality of distinguishably mass tagged binding reagents (e.g., a number of different antibodies). As there are more than 80 naturally occurring elements having more than 200 stable isotopes, the population of cells may be labeled using at least 5, at least 10, at least 20, at least 30, at least 40, at least 50, or at least 100, up to 150 or more different binding reagents (that bind to, for example different cell surface markers) that are each tagged with a different mass. After the population of cells is labeled, they are analyzed using the method described herein.

As noted above, the specific binding reagent used in the method may be any type of molecule (e.g., an antibody, a peptide-MHC tetramer, a nucleic acid (e.g., ssRNA or ssDNA), an aptamer, a ligand specific for a cell surface receptor, etc.) that is capable of specific binding to a binding partner in or on cells. The binding partner may be a protein, a nucleic acid or another type of cellular macromolecule (e.g., a carbohydrate). The binding partner may be on the cell surface, or it may be extracellular or intracellular (e.g., associated with the nucleus or another organelle, or cytoplasmic).

In certain aspects, a specific binding reagent may be an MT conjugated to a nucleic acid that hybridizes to a specific RNA and/or DNA sequence. The MT conjugated nucleic acid may be used in combination with any suitable technique for detecting a target (e.g., RNA, DNA, protein or protein complex), such as standard in-situ hybridization, In-situ hybridization utilizing branched DNA probes (e.g., as provided by Affymetrix), proximity ligation (PLA) and rolling circle amplification (e.g., as provided by Olink bioscience), and so forth. In-situ hybridization techniques, including those employing branched DNA probes are described by Monya Baker et al. (Nature Methods 9, 787-790 (2012)). Briefly, in-situ hybridization using branched DNA probes utilizes a series of ssDNA probes, where a first set of DNA probes specifically hybridizes to the target DNA or RNA sequence, and a second set of DNA probes may hybridize to a portion of the first set of DNA probes, thus expanding the number of DNA probes that can bind (indirectly) to a single DNA or RNA molecule. A third set may bind to the second set of DNA probes in a likewise manner, and so forth. One or more of the sets of DNA probes may be conjugated to a metal tag to label the target DNA or RNA molecule. Proximity ligation techniques, including detection of single RNA molecules, DNA molecules, and protein complexes are described by Weibrecht et al. (Nature Methods 9, 787-790 (2012)) which is incorporated herein by reference. Rolling circle amplification is described by Larsson et al. (Nat. Methods 1, 227-232 (2004)), which is incorporated herein by reference. Briefly, in proximity ligation followed by rolling circle amplification, a nucleic acid is hybridized to two proximal RNA or DNA strands, after which the nucleic acid is ligated and then amplified, resulting in many copies of the sequence complimentary to the nucleic acid. The complimentary sequence is therefore present in higher copy number than the original proximal RNA or DNA strands, and can be more easily detected (e.g., by a MT conjugated nucleic acid that hybridizes to the complimentary sequence). The proximal RNA or DNA stands may each be conjugated to a different antibody (e.g., where the different antibodies may each be specific for a different protein of a protein complex).

In some embodiments, cells are labeled while in a suspension, or cells in a tissue sample are labeled before dissociating the cells from the tissue, or a label is administered to a subject and labeled cells are obtained from the subject. In other embodiments, the cells are attached to the substrate, then labeled.

In certain embodiments, the cells are permeabilized before labeling, e.g., to allow the labeling agent to bind to intracellular targets. In certain embodiments, cells may be permeabilized by contacting the cells with ice-cold methanol. Methods for labeling intracellular targets using antibodies is described in, e.g., Lazarus et al (Cytometry. 1998 32:206-13), Sartor et al (Cytometry. 1994 18:119-22), Gadol et al (Cytometry 1994 15:359-70) and Far et al (Cytometry. 1994 15:327-34), and U.S. App. Pub. No. 20120178098, which are incorporated by reference for disclosure of these methods. Kits for intracellularly labeling cells for FACS analysis include the INTRACYTE™ intracellular FACS kit by Orion BioSolutions, Inc (Vista Calif.), the INTRASURE™ or FASTIMMUNE™ kits by Becton Dickinson (Franklin Lakes, N.J.) and the CYTOFIX™ or CYTOPERM™ Plus kits by PharMingen (San Diego, Calif.).

In some embodiments, a sample containing a population of cells that is suitable for use in the subject method is prepared in the same way as samples are prepared for analysis in a flow cytometer, including methods for producing a suspension of single cells and methods for labeling cells with, e.g., an antibody. Methods of preparing a sample of cells for flow cytometry analysis is described in, e.g., U.S. Pat. Nos. 5,378,633, 5,631,165, 6,524,858, 5,266,269, 5,017,497 and 6,549,876; U.S. App. Pub. Nos. US20120178098, US20080153170, 20010006787, US20080158561, US20100151472, US20100099074, US20100009364, US20090269800, US20080241820, US20080182262, US20070196870 and US20080268494; PCT publication WO99/54494; Brown et al (Clin Chem. 2000 46:1221-9), McCoy et al (Hematol. Oncol. Clin. North Am. 2002 16:229-43) and Scheffold J. Clin. Immunol. 2000 20:400-7) and books such as Carey et al (*Flow Cytometry in Clinical Diagnosis*, 4$^{th}$ Edition ASCP Press, 2007), Ormerod (*Flow Cytometry—A practical approach* 3rd Edition. Oxford University Press, Oxford, U K 2000), Ormerod (*Flow Cytometry* 2nd Edition. BIOS Scientific Publishers, Oxford, U K 1999) and Ormerod (*Flow Cytometry—A basic introduction* 2009 Cytometry Part A 75A, 2009), each of which are incorporated by reference herein.

Any of the above techniques may be used to resolve single molecular targets (e.g., individual RNA molecules, DNA molecules, proteins or protein complexes). As single molecular targets may be resolvable as discrete puncti, a combination of metal isotopes may be used to uniquely label the molecular target. In one example, the specific binding reagent may be a nucleic acid may be conjugated to a unique combination of metal isotopes. In another example, a combination of MT conjugated nucleic acids (e.g., each conjugated to a different mass tag) may be used together to label the molecular target with a unique combination of metal isotopes. As such, n number of mass tags could be combinatorially used to label $2^n$ different molecular targets, provided that the molecular targets can be spatially distinguished. The method described herein may be used to assay a sample of biological origin that contains cells, in which the amounts of certain components (e.g., protein, nucleic acid or other molecules) need to be determined.

In some embodiments, the analysis is done using a SIMS instrument (e.g. NanoTOF by Physical Electronics). Secondary Ion Mass Spectrometry is a surface sensitive technique that allows the detection and localization of the chemical composition of sample surfaces. The instrument may use a finely focused, pulsed primary ion beam to desorb and ionize molecular species from a sample surface. The resulting secondary ions are transferred into a mass spectrometer, where they are mass analyzed and quantified using standard mass analyzers (e.g., time-of-flight, magnetic sector, quadrupole, ion trap, or a combinations thereof). Displaying the mass spectra that were collected from the sample surface generates chemical images. Each pixel in the resulting image essentially represents a mass spectrum. Notably, this instrument would only require 'unit resolution'—the ability to discriminate mass reporters separated by 1 amu or more. For example, NanoTOF uses a low intensity, pulsed source that is synced with the TOF detector.

When high-speed pulsed or continuous ion beams (primary ions) are irradiated onto the surface of a solid sample at a high vacuum, a component of the surface is released into the vacuum by a desorption-ionization phenomenon. The generated positively or negatively-charged ions (secondary ions) are focused in one direction by an electrical field, and detection is performed at a remote position. When primary ions are irradiated onto the solid surface, secondary ions having various masses are generated depending on the composition of the surface of the sample. Among the secondary ions, an ion having a smaller mass flies faster than an ion having a larger mass in a TOF tube. Therefore, a measurement of a time between generation and detection of the secondary ions (flight time) enables the analysis of masses of the generated secondary ions to be performed. When primary ions are irradiated, only secondary ions generated at the outermost surface of a solid sample are released into the vacuum, so that information about the outermost surface (e.g., a depth of less than 1 nm, less than 2 nm, less than 5 nm, less than 10 nm, less than 20 nm, less than 50 nm, less than 100 nm, or more than 100 nm) of the sample can be obtained. In the TOF-SIMS, the amount of irradiated primary ions is significantly small, so that an organic compound is ionized while maintaining its chemical structure, and the structure of the organic compound can be identified from the mass spectra. The principles of secondary ion mass spectrometry are described in, e.g., Belu et al (Biomaterials. 2003 24: 3635-53), Pól et al (Histochem Cell Biol. 2010 134: 423-43) and Klitzing (Methods Mol Biol. 2013 950: 483-501), which are incorporated herein by reference.

After obtaining an array of cells on a substrate, as described above, aspects of the present disclosure include measuring, using SIMS, the abundance of the one or more mass tags at a plurality of locations occupied by the cells, thereby generating, for each individual cell measured, a set of data.

In certain embodiments, measuring the abundance of one or more mass tags at a plurality of locations occupied by the cells includes applying one or more pulses of a SIMS ion beam at a plurality of locations occupied by the cells on the substrate. In certain embodiments, applying one or more pulses of a SIMS ion beam at a plurality of locations occupied by the cells on the substrate includes applying a SIMS ion beam specifically at locations occupied by the cells on the substrate. In certain embodiments, applying one or more pulses of a SIMS ion beam at a plurality of locations occupied by the cells on the substrate includes applying a SIMS ion beam selectively at locations occupied by the cells on the substrate. In certain embodiments, applying one or more pulses of a SIMS ion beam at a plurality of locations occupied by the cells on the substrate includes applying a SIMS ion beam preferentially at locations occupied by the cells on the substrate. In some embodiments, when one or more pulses of a SIMS ion beam are applied to a plurality of locations occupied by the cells on the substrate to measure the abundance of the one or more mass tags associated with the cells, the SIMS ion beam is not applied to a location on the substrate that is not occupied by a cell. Thus, in certain embodiments, measuring the abundance of the one or more mass tags at a plurality of locations occupied by the cells includes not measuring the abundance of the one or more mass tags at a location not occupied by the cells.

In certain embodiments, measuring the abundance of one or more mass tags at a plurality of locations occupied by the cells on an array includes applying one or more pulses of a SIMS ion beam at a plurality of pre-determined locations that are occupied by cells on the substrate. In such instances, the array is an addressable array, wherein the substrate is pattern-coated and the spatial distribution of attachment sites for cells are pre-determined, as described above.

In certain embodiments, measuring the abundance of one or more mass tags at a plurality of locations occupied by the cells of an array includes determining the locations occupied by the cells of the array on the substrate before applying one or more pulses of a SIMS ion beam at the locations determined to be occupied by the cells. Any convenient method may be used to determine the location of cells of the array on the substrate. In certain embodiments, the locations occupied by the cells of the array on the substrate is determined by imaging the array before measuring the abundance of the one or more mass tags at a plurality of locations determined to be occupied by the cells of the array. In certain embodiments, the determining. e.g., imaging, is performed before the substrate is placed in a SIMS instrument. In certain embodiments, the determining, e.g., imaging, is performed after the substrate is placed in a SIMS instrument, but before measuring the abundance of the one or more mass tags at a plurality of locations occupied by the cells of the array. Thus, in certain embodiment, the imaging includes a rapid survey scan of the substrate using optical imaging, electron imaging, or SIMS. In certain embodiments, the imaging includes acquiring an optical image, acquiring an electron image, or using low resolution SIMS. In certain embodiments, the imaging to determine the location of cells of the array on the substrate using SIMS includes using a rapid, survey scan of the substrate using SIMS. Thus in certain embodiments, a low resolution SIMS includes a rapid survey scan of the substrate using SIMS. In some embodiments, the rapid survey scan of the substrate using SIMS is achieved by applying a SIMS ion beam at locations on the substrate without regard to whether a cell is present at any given location. In certain embodiments, the rapid survey scan of the substrate using SIMS is achieved by scanning the substrate with a SIMS ion beam without regard to whether a cell is present at any given location. In some embodiments, the rapid survey scan of the substrate using SIMS is achieved by applying one or more pulses of a SIMS ion beam at regular intervals across the surface of the substrate. In some embodiments, the rapid survey scan of the substrate using SIMS is achieved by applying a continuous SIMS ion beam across the surface of the substrate. In some embodiments, the cells may be labeled with a mass tag that is configured to associate non-specifically with the cells before carrying out the survey scan of the substrate using low resolution SIMS. In certain embodiments, the location of 50% or more, e.g., 55% or more, 60% or more, 65% or more, 70% or more, 75% or more, 80% or more, 85% or more, 90% or more, 95% or more, 97% or more, or 100% of the cells on the substrate is determined using the rapid survey imaging scan of the substrate.

In certain embodiments, the image of the substrate obtained by the rapid survey scan of the substrate using optical imaging, electron imaging, or SIMS may be analyzed to determine the location of the cells of an array on a substrate. In certain embodiments, the image of the substrate obtained by the rapid survey scan of the substrate using optical imaging, electron imaging, or SIMS may be analyzed to identify locations on the substrate that are occupied by two or more cells that are not separated from each other. Thus, in certain embodiments, the image of the substrate obtained by the rapid survey scan of the substrate using optical imaging, electron imaging, or SIMS may be analyzed to identify cell clumps, which may not be identified based solely on the measurement of the abundance of one or more mass tags at a plurality of locations occupied by the cells of the array using SIMS. In some embodiments, locations on the substrate that are occupied by two or more cells that are not separated from each other are removed from further analysis, e.g., the abundance of the one or more mass tags at such locations are not measured, the data from such locations are not outputted, or cells from such locations are not analyzed further by, e.g., recovering the cells and sequencing the nucleic acids in the cells.

Figure 2:
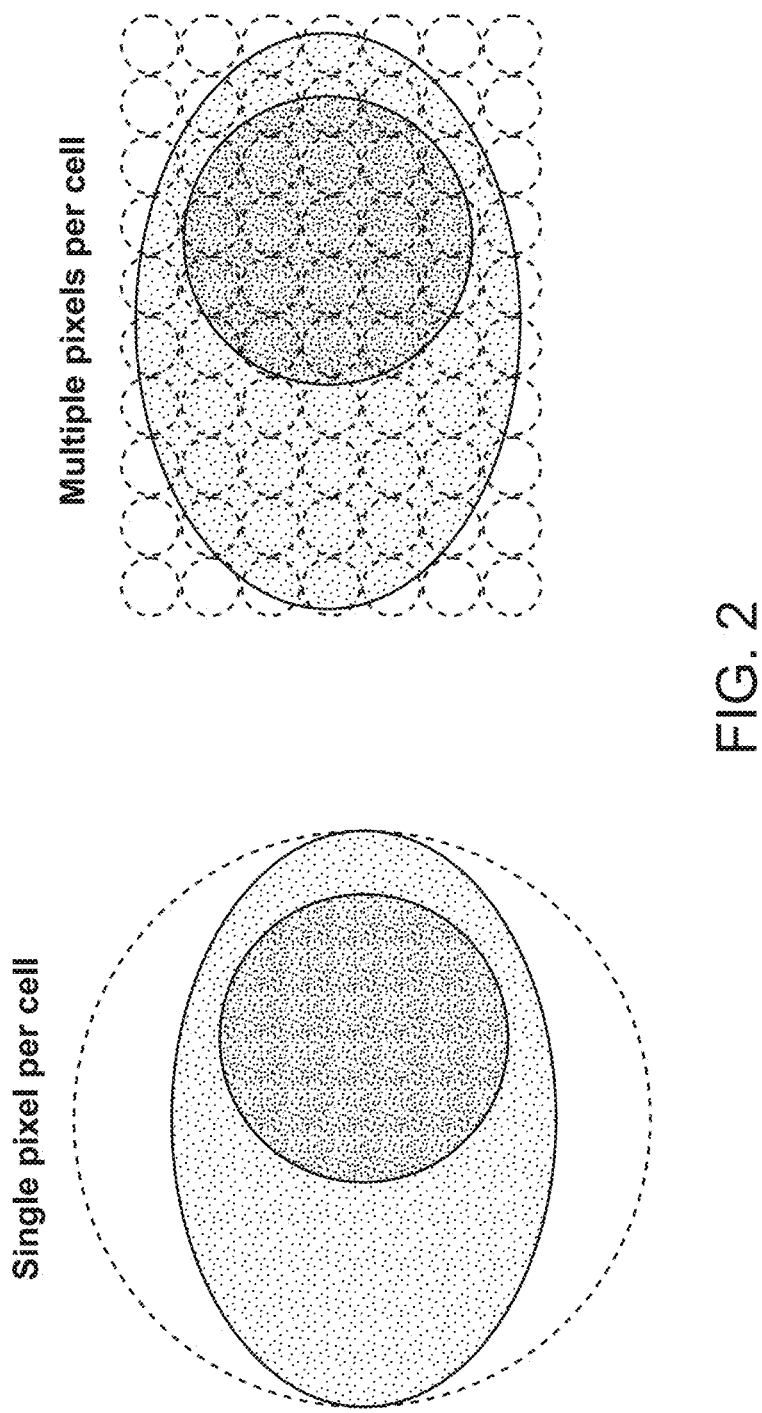
FIG. 2 shows schematic representations of primary ion beam diameters relative to a cell, according to embodiments of the present disclosure.

In certain embodiments, the measuring step includes applying a SIMS ion beam with a diameter equal to or greater than half the diameter of an individual cell to measure the abundance of the one or more mass tags on a whole cell basis (FIG. 2, left panel). Thus, in certain embodiments, the measuring step includes applying a pulse of a SIMS ion beam that has sufficient resolution to obtain a reliable measurement of the abundance of the one or more mass tags for the cell. By reliable measurement is meant that, e.g., at least the relative abundance of the labeled target molecule with which the mass tag associates across individual cells is reflected in the measured abundance of the one or more mass tags. A reliable measurement may also include measurement of the amount of the labeled target molecule that is proportional to the amount of the labeled target molecule with which the mass tag associates. In certain embodiments, the width of the beam used to measure the abundance of the one or more mass tags on a whole cell basis is equal to or greater than 40%, e.g., equal to or greater than 50%, equal to or greater than 60%, equal to or greater than 80%, equal to or greater than 100%, equal to or greater than 120%, equal to or greater than 150%, and may be up to 200% of the average diameter of the cells. In certain embodiments, the width of the beam used to measure the abundance of the one or more mass tags on a whole cell basis is in the range of 40% to 200%, e.g., 50% to 150%, or 80% to 120% of the average diameter of the cells. In certain embodiments, the width of the beam used to measure the abundance of the one or more mass tags on a whole cell basis is in the range of 1 µm to 50 µm, e.g., 1.5 µm to 40 µm, 1.75 µm to 30 µm, including 2 µm to 20 µm. In certain embodiments, the width of the beam used to measure the abundance of the one or more mass tags on a whole cell basis is 1 µm or more, e.g., 1.5 µm or more, 2 µm or more, 2.5 µm or more, or 3 µm or more, and may be 50 µm or less, e.g., 40 µm or less, 35 µm or less, 30 µm or less, 25 µm or less, or 20 µm or less.

In certain embodiments, the measuring step includes applying a plurality of pulses of a SIMS ion beam at different sites of an individual cell of an array to obtain measurements of the abundance of the one or more mass tags at the different sites (FIG. 2, right panel). In certain embodiments, the different sites of an individual cell may include different spatial positions within a location occupied by a cell of the array on a substrate. In some cases, the different sites may correspond to different locations within and/or across subcellular structures or compartments of a cell. Thus, in certain embodiments, the measuring step includes applying a plurality of pulses of a SIMS ion beam that has sufficient resolution at different sites of an individual cell to obtain a reliable measurement of the abundance of the one or more mass tags at the different sites. In some cases, the method includes scanning a SIMS ion beam (e.g., a continuous or quasi-continuous SIMS ion beam) across different sites within an individual cell of an array to obtain measurements of the abundance of the one or more mass tags at the different sites. In certain embodiments, the width of the beam used to measure the abundance of the one or more mass tags at different sites of an individual cell is equal to or less than 50%, e.g., less than 45%, less than 40%, less than 30%, less than 20%, less than 10%, less than 5%, or less than 1% of the average diameter of the cells. In certain embodiments, the width of the beam used to measure the abundance of the one or more mass tags at different sites of an individual cell is in the range of 50% to 0.1%, e.g., 20% to 0.2%, 10% to 0.5%, or 5% to 0.5% of the average diameter of the cells. In certain embodiments, the width of the beam used to measure the abundance of the one or more mass tags at different sites of an individual cell is in the range of 10 nm to 1500 nm, e.g., 50 nm to 1250 nm, 100 nm to 1100 nm, 200 nm to 1000 nm, including 300 nm to 750 nm. In certain embodiments, the width of the beam used to measure the abundance of the one or more mass tags at different sites of an individual cell is 1 nm or more, e.g., 5 nm or more, 10 nm or more, 20 nm or more, 50 nm or more, 75 nm or more, 100 nm or more, 150 nm or more, or 200 nm or more, and may be 2 µm or less, e.g., 1.5 µm or less, 1.2 µm or less, 1.1 µm or less, 1 µm or less, or 0.75 µm or less.

Figure 3:
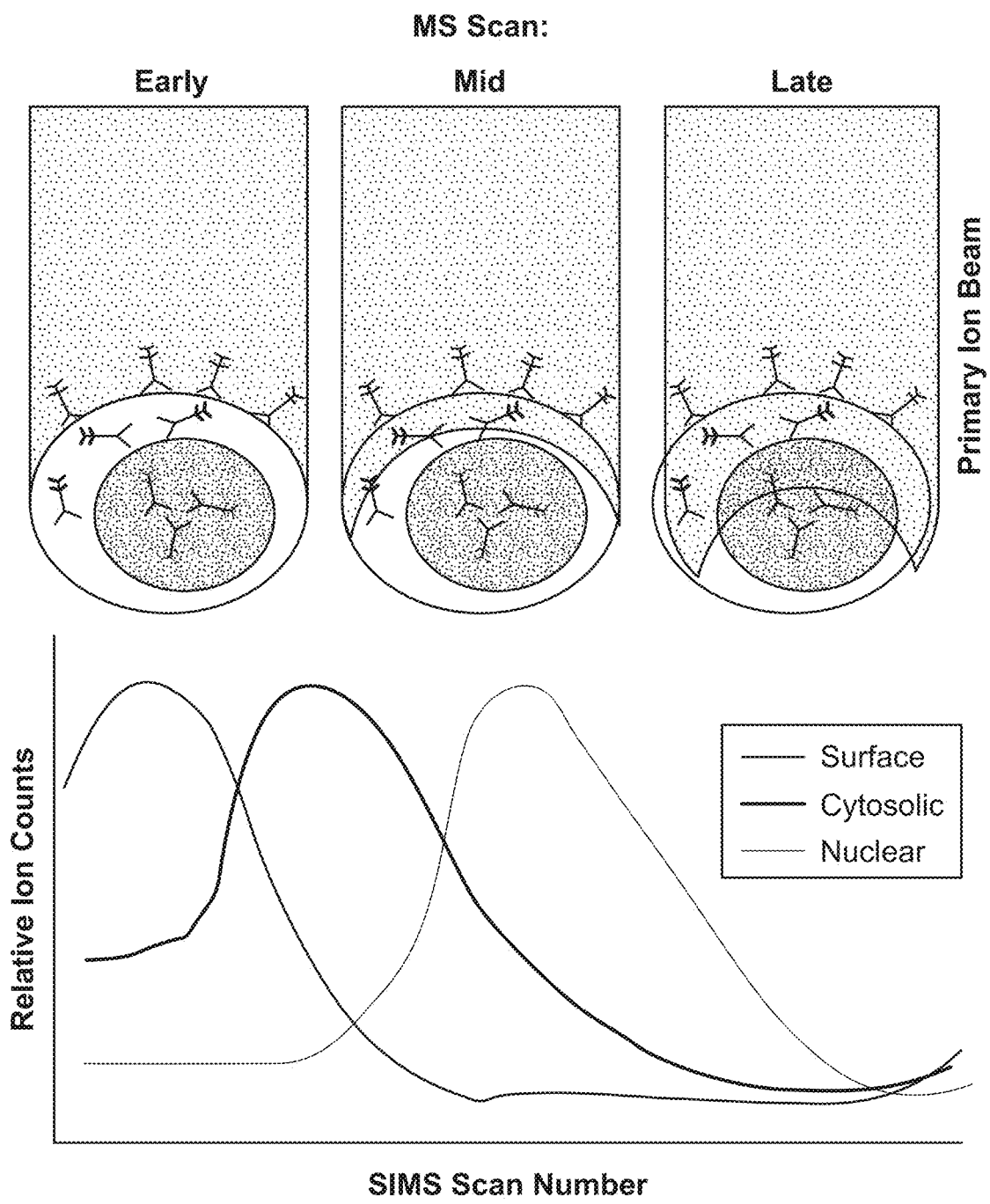
FIG. 3 shows a schematic representation of single cell mass tomography using SIMS analysis, according to an embodiment of the present disclosure.
Figure 4:
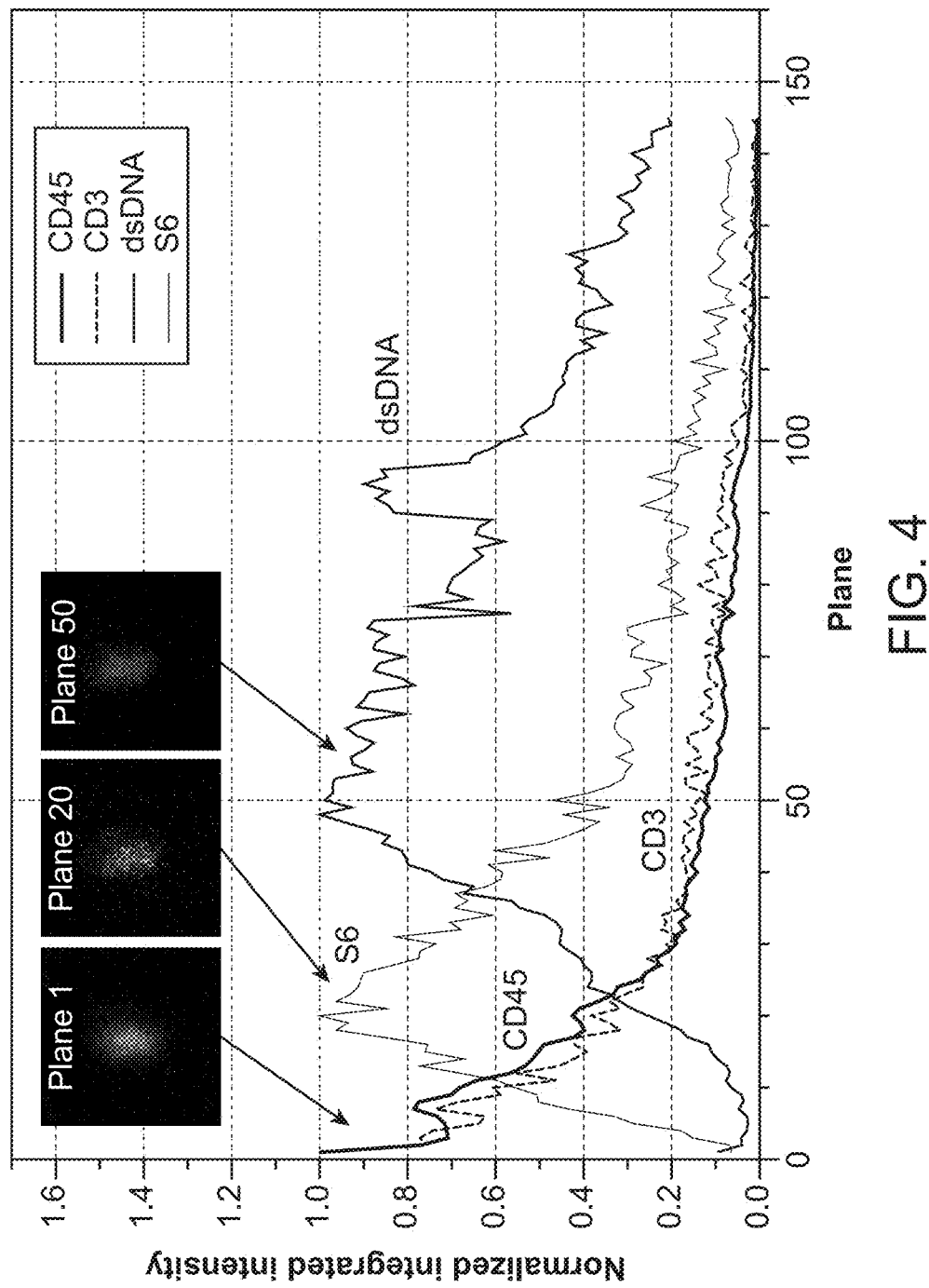
FIG. 4 shows a depth profile of the abundance of mass tags configured to label different subcellular structures in a T-cell, according to an embodiment of the present disclosure.

In certain embodiments, the measuring step includes applying one or more pulses of a SIMS ion beam to obtain a measurement of the abundance of the one or more mass tags at different depths (FIGS. 3 and 4). Thus in certain embodiments, the measuring step includes applying one or more pulses of a SIMS ion beam that has a primary ion current, sputtering yield, ionization efficiency and dwell time sufficient to obtain a measurement of the abundance of the one or more mass tags at different depths. In some cases, one or more SIMS ion beams are scanned across different sites within an individual cell of an array to obtain a measurement of the abundance of the one or more mass tags at different depths. By "depth" is meant along the axis perpendicular to the surface of the substrate (z-axis) on which the array of cells is attached, in a proximal to distal direction relative to the ion beam source. In certain embodiments, the measuring step includes applying one or more pulses of a SIMS ion beam to obtain a measurement of the abundance of the one or more mass tags at a depth resolution in the range of 0.01% to 100%, e.g., 0.02% to 50%, 0.05% to 20%, 0.1% to 10%, including 0.5% to 5% of the average depth of the cells. In certain embodiments, the measuring step includes applying one or more pulses of a SIMS ion beam to obtain a measurement of the abundance of the one or more mass tags at a depth resolution in the range of 1 nm to 50,000 nm, e.g., 2 nm to 10,000 nm, 2 nm to 1,000 nm, 3 nm to 500 nm, 3 nm to 100 nm, 4 nm to 50 nm, 4 nm to 20 nm, including 5 nm to 10 nm. In some embodiments, the measuring step includes applying one or more pulses of a SIMS ion beam to obtain a measurement of the abundance of the one or more mass tags of the entire cell depth.

In certain embodiments, the measuring step includes applying one or more pulses of a SIMS ion beam that has a primary ion current, sputtering yield, ionization efficiency and dwell time sufficient to obtain a measurement of the abundance of the one or more mass tags at a superficial location of the cells, which may correspond to the plasma membrane on the side of the cell proximal to the ion beam source. Thus in certain embodiments, the measuring step includes applying one or more pulses of a SIMS ion beam to obtain a measurement of the abundance of the one or more mass tags associated with the plasma membrane of the cells. In some embodiments, the measuring step includes applying one or more pulses of a SIMS ion beam to obtain a measurement of the abundance of the one or more mass tags at a sampling depth of 20 nm or less, e.g., 15 nm or less, 10 nm or less, 8 nm or less, 6 nm or less, or 5 nm or less, and in some cases may have a sampling depth of 1 nm or more, e.g., 2 nm or more, 3 nm or more, 5 nm or more, 7 nm or more, or 10 nm or more from the surface of the cell proximal to the ion beam source. In some embodiments, the measuring step includes applying one or more pulses of a SIMS ion beam to obtain a measurement of the abundance of the one or more mass tags at a sampling depth in the range of 1 to 20 nm, e.g., 2 to 15 nm, 3 to 13 nm, 4 to 11 nm, or 5 to 10 nm from the surface of the cell proximal to the ion beam source.

In certain embodiments, the measuring step includes measuring the abundance of one or more mass tags at a plurality of depths as the SIMS ion beam etches through the individual cell (FIGS. 3 and 4). Thus, in some instances, the measuring step includes applying a plurality of SIMS ion beam pulses at different depths of the cell as the SIMS ion beam etches through the cell, to obtain three dimensional (3D) measurements of the abundance of the one or more mass tags associated with the cell. The depth resolution of the measurements, i.e., resolution of the measurements along the z-axis, may vary according to the desired resolution and speed of data acquisition, and will depend on the primary ion current, sputtering yield, ionization efficiency and dwell time of the ion beam. Thus, in some instances, the measuring step includes applying a plurality of pulses of a SIMS ion beam that has a primary ion current, sputtering yield, ionization efficiency and dwell time sufficient to obtain a measurement of the abundance of the one or more mass tags at a plurality of sampling depths with depth resolution sufficient to determine the subcellular localization of the one or more mass tags. In certain embodiments, the depth resolution is 0.01% or more, e.g., 0.05% or more, 0.1% or more, 0.2% or more, 0.3% or more, 0.5% or more, 1% or more, 1.5% or more, 2% or more, 4% or more, 6% or more, 8% or more, 10% or more, 20% or more, 30% or more, and may be 60% or less, e.g., 50% or less, 40% or less, 30% or less, 20% or less, 10% or less, 5% or less, 3% or less, 1% or less, or 0.5% or less, of the average depth of the cells.

In certain embodiments, the depth resolution is in the range of 0.01% to 50%, e.g., 0.03% to 30%, 0.04% to 20%, 0.05% to 15%, 0.01% to 10%, 0.2% to 5%, or 0.1% to 5% of the average depth of the cells. In certain embodiments, the depth resolution is 1 nm or more, e.g., 2 nm or more, 5 nm or more, 10 nm or more, 20 nm or more, 30 nm or more, 40 nm or more, 50 nm or more, 100 nm or more, 200 nm or more, 300 nm or more, 400 nm or more, 500 nm or more, and may be 5,000 nm or less, e.g., 1,000 nm or less, 800 nm or less, 600 nm or less, 400 nm or less, 200 nm or less, 100 nm or less, or 50 nm or less. In certain embodiments, the depth resolution is in the range of 1 nm to 5,000 nm, e.g., 2 nm to 1,000 nm, 3 nm to 500 nm, 4 nm to 100 nm, or 5 to 50 nm.

In certain embodiments, the subject method is a rapid, high throughput method of analyzing a population of cells. In certain embodiments, the measuring step includes applying one or more pulses of a SIMS ion beam that has a beam width, primary ion current, sputtering yield, ionization efficiency and dwell time sufficient to rapidly obtain a measurement of the abundance of the one or more mass tags of cells of an array. In certain embodiments, measurement of the abundance of the one or more mass tags associated with cells of an array is acquired at a rate in the range of 1 cell/s to 100,000 cells/s, e.g., 1 cell/s to 2,000 cells/s, 5 cells/s to 1,000 cells/s, 10 cells/s to 1,000 cells/s, 2,000 cells/s to 50,000 cells/s, 3,000 cells/s to 30,000 cells/s, or 4,000 cells/s to 20,000 cells/s. In certain embodiments, measurement of the abundance of the one or more mass tags localized to the surface proximal to the ion beam source of cells is acquired at a rate in the range of 2,000 cells/s to 100,000 cells/s, e.g. 4,000 cells/s to 50,000 cells/s, 6,000 cells/s to 20,000 cells/s, or 8,000 cells/s to 15,000 cells/s. In certain embodiments, 3D measurement of the abundance of the one or more mass tags associated with a plurality of depths through the cell is acquired at a rate in the range of 1 cell/s to 5,000 cells, e.g., 1 cell/s to 2,500 cells, 5 cells/s to 2,000 cells, 10 cells/s to 1,500 cells, including 10 cells/s to 1,200 cells.

In some instances, the measuring step of the present method includes applying one or more pulses of a SIMS ion beam that has a beam width, primary ion current, sputtering yield, ionization efficiency and dwell time sufficient to obtain a measurement of the abundance of the one or more mass tags localized to the surface of a cell of an array, outputting a first set of data for one or more of the cells analyzed and determining if any given cell is of interest based on the measured abundance of the one or more mass tags localized to the surface of the cell in the first set of data. Then, the method may include applying a plurality of SIMS ion beam pulses at different depths of a cell as the SIMS ion beam etches through the cell, to obtain three dimensional (3D) measurements of the abundance of the one or more mass tags associated with the cell, if the cell is determined to be of interest, to generate a second set of data for one or more of the cells determined to be of interest. In some cases, a cell may be of interest if it is associated with a mass tag that is configured to bind to a cell-surface feature, e.g., a cell-surface protein or receptor, if the feature is present on the surface of the cell. In such an embodiment, only cells of interest will have a full depth profile of mass tags associated with the cell.

In certain embodiments, the subject method is a highly sensitive method of analyzing a population of cells. In certain embodiments, the ionization efficiency of the one or more mass tags labeling the cells, when impinged upon by the SIMS ion beam, is 0.01% or more, e.g., 0.05% or more, 0.1% or more, 0.5% or more, 1% or more, 1.5% or more, 2% or more, 3% or more, 4% or more, 5% or more, 6% or more, 7% or more, 8% or more, 9% or more, or 10% or more, and may be 15% or less, e.g., 12% or less, or 10% or less. In certain embodiments, the ionization efficiency of the one or more mass tags labeling the cells, when impinged upon by the SIMS ion beam, is in the range of 0.01% to 15%, e.g., 0.05% to 12%, including 0.1% to 10%. In certain embodiments, the SIMS ion beam is a beam of ions that has a high ionization yield, such as, but not limited to, an oxygen ion beam. In some embodiments, the measuring step includes applying one or more pulses of a SIMS ion beam to detect a single molecule of the mass tagged label associated with the cell. As such, the measuring step includes applying one or more pulses of a SIMS ion beam that has a beam width, primary ion current, sputtering yield, ionization efficiency and dwell time sufficient to detect a single molecule of the mass tagged label associated with the cell.

In some embodiments, the SIMS ion beam position and the mass information detected by the mass spectrometer are coordinated using a synchronizer, so as to correlate a detected mass tag to its location in a two dimensional or three dimensional space (e.g., location on an array corresponding to an individual cell, different sites within an individual cell, etc.).

After the initial data is obtained, the data may be processed. The analyzed data may be further processed to identify whole cell features or subcellular features of individual cells. Next the data that corresponds to each of the individual cells, or a subcellular feature thereof, are integrated to provide, for each cell, values that represent the amount of each of the mass tags of each cell of the array. This step of the method results in a data set that contains, for each cell, measurements of the amount of each of the mass tags that are associated with the cell. This concept is illustrated in the table shown below.

|        | Tag 1 | Tag 2 | Tag 3 | Tag 4 | Tag 5 |
|--------|-------|-------|-------|-------|-------|
| Cell 1 | 0.1   | 0.1   | 5     | 3     | 1     |
| Cell 2 | 0.2   | 0.4   | 4     | 0.1   | 0.1   |
| Cell 3 | 10    | 0.1   | 0.2   | 0.3   | 5     |

This data allows one to categorizing the cells in the array. For example, in the example shown in the table above, the three cells are likely to be different types of cells because they have different profiles of mass tags where the profile identifies the category. In particular cases, this information may be used to provide a false-color image in which each of the cells is color-coded by their category. As such, this method may comprise displaying an image of the array, in which the cells are color-coded by their category. In particular embodiments, in any one pixel of the image, the intensity of the color of the pixel correlates with the magnitude of the signals obtained for that pixel by applying a SIMS ion beam at the location on the substrate. In these embodiments, the resulting false color image may show color-code cells in which the intensity of the color in any single pixel of a cell correlates with the amount of specific binding reagent that is associated with the corresponding area in the array or cell. In some embodiments, the data categorizing the cells in the array may be converted into a .FCS format and analyzed and/or visualized using a standard cytometry data analysis platform.

In some cases, the data is processed to generate a data set that contains, for each cell, measurements of the amount of each of the mass tags that are associated with one or more distinct subcellular compartments within the cell. The subcellular compartments may be any suitable subcellular structures, such as, without limitation, the plasma membrane, cell wall, cytoplasm, nucleus, nuclear membrane, chromosomes, centrosomes, other organelles (endoplasmic reticulum, golgi, mitochondria, chloroplasts, phagosomes, centrioles, lysosomes, vacuoles, nucleolus, etc.). In some cases, the subcellular structure with which the mass tag associates is known. In some cases, the amount of a first mass tag that associates with a distinct subcellular structure is determined using one or more second mass tags that localize to a known subcellular structure of the cell, and correlating the position at which the first mass tag is detected with the location at which the second mass tag representing the subcellular structure is detected, as described further below. Thus, in some cases, the data set contains, for each cell of an array of cells, a profile of mass tag abundance at the whole cell level, and/or for one or more cellular compartments, e.g., subcellular structures, within the cell. In some embodiments, this data set may be present as a table in which, each column is a cell or subcellular compartment and each row is a summarized statistic (e.g., the average or median signal) for each mass tag used, or vice versa.

As the original measurement using SIMS may only result in partial removal of individual cells (e.g., at a depth on the nanometer scale), the cells may be re-analyzed to generate an additional data set having measurements of the abundance of one or more mass tags across the area that was originally measured. For example, the original measurement using SIMS may be used to identify a subpopulation of cells of interest in the array. Such a SIMS analysis may be lower resolution and may therefore be more rapid, measure the mass tag abundance in a larger area at a time, and/or may result in removal of less of individual cells. The re-analysis using SIMS may be a higher resolution measurement of the abundance of metal tags in the area or areas of interest. Alternatively or in addition, multiple measurements across the same area may be used to produce a 3 dimensional image (e.g., compiled from the individual 2 dimensional data sets), as described above. In certain aspects, areas of interest identified by an original measurement using SIMS may be analyzed further after isolation of the cells of interest from the array, e.g., such as by laser capture micro dissection, as described herein.

The method described herein may include normalization as a means of standardizing data obtained across arrays and/or time-points (e.g., to enable quantitative cross-array comparison). In certain aspects, normalization of ionization and/or overall measurement efficiency may be performed using standardized metal particles or suspension present on the substrate. The standardized metal particles or suspension may have a known amount of one or more mass tags, and the resulting measurement of the one or more mass tags may be used to normalize the measurements of other mass tags in the cells. For example, normalization beads may be used to calibrate the system or normalize data obtained by the subject method. Normalization of mass cytometry data using bead standards is described by Rachel Fink et al. (Cytometry A. 83(5):483-94(2013)), which is incorporated herein by reference, and is applicable to the subject method which also utilize time of flight mass spectrometry. Alternatively or in addition, ionization and/or measurement efficiency may be normalized according to any of the above-mentioned stains. For example, measurements of a mass tag used to stain the ER may be normalized to the overall intensity of that mass tag in a given area, in the cell, or across multiple cells in the array.

Figure 5:
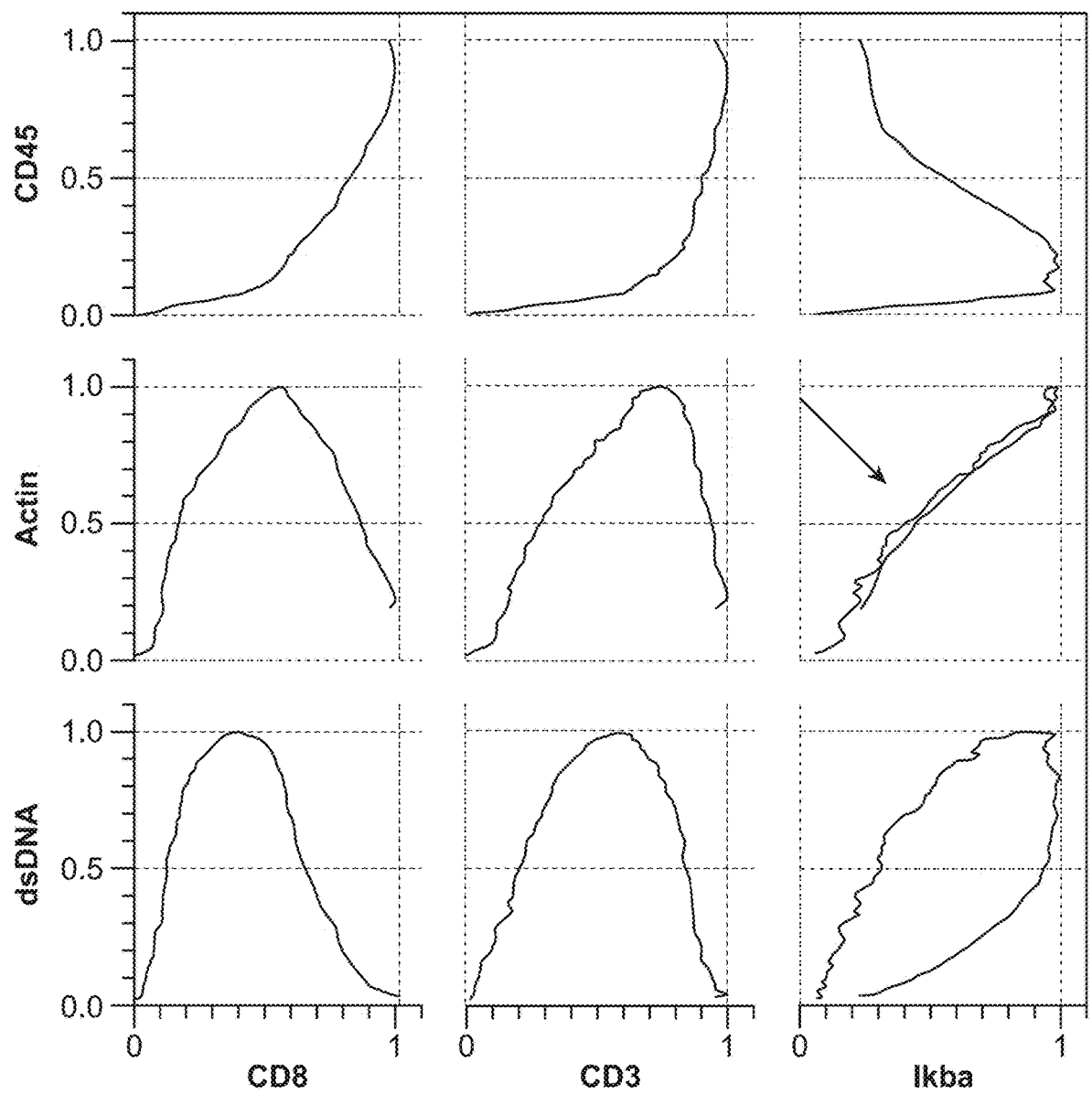
FIG. 5 shows subcellular colocalization of different masstag labels, according to an embodiment of the present disclosure.

Normalization may also be used to account for the effects of, for example, degree of tissue fixation, retention of protein, and staining efficiency with specific binding reagents. Mass tags conjugated to well-characterized antibodies that bind molecular targets stably expressed across a wide range of cell types and subcellular sites may be used for normalization. Such antibodies include, without limitation, antibodies to housekeeping proteins (such as GAPDH, HSP90, beta-actin and beta-tubulin), dsDNA and histone H3. Through correlation of localization standards (i.e. dsDNA—nucleus, GAPDH—cytosol) that are coincident in a given SIMS analysis plane the cellular localization or relative distribution of unknown targets with unique mass tags can be inferred (FIG. 5). These inferred relative expression values can be extrapolated on a cell by cell basis as with the total expression information described above.

As discussed above, the method of the present disclosure allow for a multiplexed approach. Multiple mass tags may be measured to determine the abundance of multiple molecular targets (e.g. specific proteins, DNA, RNA, etc.) as well as biologic features of interest in the cells (e.g., cell structure, cellular organelles, cellular fractions, etc.). In addition, mass tag measurements may be normalized according to any of the above-described embodiments. The large number of discrete mass tags enables multiplexing of more than 2, 5, 10, 20, 30, 40, 50, 60, 70, 80, 100 or more different mass tags in a single area. Multiple mass tags (e.g., conjugated to antibodies against complementary epitopes of the same molecular target) may be used for redundancy so as to increase confidence in a measurement of a specific molecular target. Further multiplexing may be achieved by using identical mass tags to label two or more spatially distinct targets or features of interest. Alternatively or in addition, a unique combination of metal tags may be used to identify a spatially distinct target or feature of interest.

Following measurement of the abundance of the one or more mass tags at a plurality of locations occupied by the cells using SIMS, aspects of the present disclosure include outputting the set of data for each of the cells analyzed. In certain embodiments, the data set contains the identity, abundance and location of the one or more mass tags. Thus in certain embodiments, the identity, abundance and/or location of the one or more mass tags for each cell is provided in the output. The data may be output in any convenient form. In certain embodiments, the data is output on an output device, such as a computer monitor, a computer-readable medium, a printer, etc.

In certain embodiments, the subject method of analyzing a population of cells further includes labeling cells with a first mass tag and a second mass tag, wherein the first mass tag localizes to a known subcellular structure of the cell, measuring the abundance of the first and second mass tags at different sites of an individual cell of the array, and determining the subcellular localization of the second mass tag based on the measured abundance of the first and second mass tags. The first mass tag may be any convenient mass tag that is a part of or conjugated with a first moiety, e.g., a stain, an antibody or an oligonucleotide, that localizes the mass tag to a known subcellular structure. The subcellular structure may include, but is not limited to, the plasma membrane, cell wall, cytoplasm, nucleus, nuclear membrane, chromosomes, centrosomes, other organelles (endoplasmic reticulum, golgi, mitochondria, chloroplasts, phagosomes, centrioles, lysosomes, vacuoles, nucleolus, etc.). In some instances, the localization of the second mass tag that is a part of or conjugated with a second moiety is not known. In such instances, the subcellular localization of the first mass tag may be used as a reference point to determine the subcellular localization of the second mass tag, and therefore the subcellular localization of the second moiety or a target molecule with which the second moiety associates. In some cases, the amount of the second mass tag localized to the subcellular structure may be measured using the subcellular localization of the first mass tag as a reference point.

In certain embodiments, where less than the entire cell is impinged upon by the SIMS ion beam, the remaining portion of the cell may be recovered for further analysis. Thus in certain embodiments, the subject method of analyzing a population of cells further includes identifying one or more cells of interest based on the obtained set of data, and recovering the identified cells for further analysis. In certain embodiments, the identifying step includes classifying cells of an array of cells on a substrate analyzed by SIMS, as described above, based on the abundance of one or more mass tags associated with the cell or a subcellular location of the cell, such as the plasma membrane, and selecting cells that meet one or more criteria. In some embodiments, one or more cells may be selected based on the distribution of one or more mass tags across the entire population of the analyzed cells on a histogram, as described further below.

Recovering one or more cells of interest may be done using any convenient method. In certain embodiments, the recovering includes aspirating the one or more cells with a micropipette. In certain embodiments, the recovering includes laser micro dissection.

The further analysis may include any suitable analysis. In some embodiments, further analysis includes sequencing, including next generation sequencing of the genome, transcriptome, etc. of the cells of interest.

Method of Analyzing a Test Population of Cells

Aspects of the present disclosure further includes a method of analyzing a test population of cells, e.g., a method of analyzing a population of cells that have been contacted with a test agent to determine the effect of the test agent on the cells, or a method of analyzing a population of cells that have been obtained from a pathological tissue in a patient to diagnose a disease, etc. In certain embodiments, the method includes obtaining an array of cells from a test population on a substrate, wherein the cells are labeled with one or more mass tags and are separated from one another; measuring, using SIMS, the abundance of the one or more mass tags at a plurality of locations occupied by the cells, thereby generating, for each individual cell measured, a set of data; generating a histogram showing the distribution of the mass tags across the test population of cells; and comparing the histogram to a reference histogram obtained from a reference population of cells. Methods for obtaining an array of cells on a substrate, wherein the cells are labeled with one or more mass tags and are separated from one another, and measuring, using SIMS, the abundance of the one or more mass tags at a plurality of locations occupied by the cells, thereby generating, for each individual cell measured, a set of data are as described above.

The test population of cells may be any suitable test population of cells. In some embodiments, the test population of cells is contacted with a test agent, e.g., a drug, an antibody, a nucleic acid, a virus, etc. In some embodiments, the test population of cells is contacted with a test agent in vitro. In some embodiments, the test population of cells is contacted with a test agent in vivo, by, e.g., administering the test agent to a subject, and the test population of cells is obtained from the subject following administration of the test agent. In certain embodiments the test population cells is obtained from a diagnosed with a condition, e.g., a disease, such as cancer. In such instances, the test population cells may be a biopsy of pathological tissue, a pathological tissue removed during surgery, a peripheral blood draw, etc.

The histogram showing the distribution of the mass tags across the test population of cells may be generated using any suitable method. In certain embodiments, the histogram is a one dimensional histogram showing the distribution of one mass tag across the test population of cells. In other embodiments, the histogram is a multi-dimensional histogram showing the distribution of two or more mass tags across the test population of cells. In some embodiments, the histogram is a two-dimensional histogram.

The reference population of cells may be any suitable population of cells. In certain embodiments, when the test population of cells is contacted with a test agent, the reference population of cells may be obtained from the same population of cells as the test population of cells but which has not been contacted with the test agent, or may be a different population of cells that has not been contacted with the test agent. In certain embodiments, the reference population of cells may be obtained from the same population of cells as the test population of cells but is contacted with a different amount, e.g., a lower dose, of the test agent, or may be a different population of cells that has been contacted with a different amount, e.g., a lower dose, of the test agent than the test population of cells. In such instances, when the test population of cells is obtained from a subject to which a test agent has been administered, the reference population of cells maybe cells obtained from the same subject before the test agent is administered. In certain embodiments, when the test population of cells is obtained from pathological tissue of a patient, e.g., cancerous tissue, the reference population of cells may be obtained from tissue from a healthy subject. Comparing the histogram generated from an analysis of cells from the test population with a reference histogram generate from an analysis of cells from the reference population may provide diagnostic or prognostic information about a disease, efficacy of treatment in a patient, or a readout of the effect of a test agent on the population of cells.

In certain embodiments, the subject method may further include, after generating a histogram from an analysis of a test population of cells and a reference histogram from an analysis of a reference population of cells, identifying one or more cells of interest based on a threshold value for the abundance of the one or more mass tags. In certain embodiments, the threshold value is determined by analyzing the histogram from the test population of cells. In certain embodiments, the threshold value is determined by analyzing a reference histogram from an analysis of a reference population of cells, as described above. Such an analysis may include determining the mean, modes, or any other suitable statistical value calculated from the distribution of the mass tags across a population of cells. In certain embodiments, upon determining an appropriate threshold value for the abundance of the one or more mass tags as described above, one or more cells of interest may be identified based on whether the abundance of the one or more mass tags in a given cell of the test population is above or below the threshold value.

In one example, the test sample is blood. In this example, the test sample may be contacted with a test agent ex vivo or in vivo. The reference sample of blood may not have been contacted with the test agent or may have been contacted with a different amount of the test agent, for example. In one embodiment, both the test and reference samples may have been contacted with the same amount of the test compound, but at different times or for different durations. The test and reference samples may be obtained from the same subject, or from different subjects. The subject may have fasted for at least 8-12 hours, or, in certain cases, the method may be performed before, during or after exercise, for example. The method may be coupled with another medical test to provide an evaluation of the health of the subject. In some cases, the mechanism of action a test agent may be unknown.

In one exemplary embodiment, separate aliquots of blood from the same individual are contacted with two or more amounts of a test agent. The contacted blood may be assayed using the method described above.

In another exemplary embodiment, separate aliquots of blood from the same individual are contacted with: a) a test agent and b) a control solution that does not contain the test agent. The contacted blood may be assayed using the method described above, and the effect of the compound on the cells is determined.

In these embodiments, the degree to which the test sample and control sample differ may be determined by comparing, for example, a geometric mean of the results obtained from a test sample to a geometric mean of the results obtained from a reference sample, for one or more labels. A greater difference between the geometric means indicates that the agent has a greater effect. Relative to the geometric mean of a sample that had not been contacted with the compound, a bioactive compound may alter the geometric mean by at least 5%, at least 10%, at least 20%, or at least 50%. In particular embodiments, the compound may lead to a decrease of at least 10%, at least 20%, at least 50%, at least 70% or at least 80% in the geometric mean for a label. In other embodiments, the compound may lead to an increase of at least 10%, at least 20%, at least 50%, at least 70%, at least 100% or at least 200% or at least 500% or more in the geometric mean of a label.

As noted above, the test agent may be administered in vivo, in which case, the contacting may comprise administering the test agent to a subject and then drawing blood from the subject after a specified period of time (e.g., from 5 minutes to 1 hr, 1 hr to 12 hr, 12 hr to 24 hr or 24 hr to 1 week or more) prior to analysis. In ex vivo applications, the contacting may comprise drawing blood from a subject and then contacting the test agent with the drawn blood for a specified period of time (e.g., from 5 minutes to 1 hr, 1 hr to 12 hr, 12 hr to 24 hr or 24 hr to 1 week or more) prior to analysis.

System

Further aspects of the present disclosure include systems that find use in performing the subject method, as described above. Thus, aspects of the present disclosure include an automated system for analyzing an array of cells, the system containing a SIMS system containing a holder for retaining a substrate comprising an array of cells, wherein the cells are labeled with one or more mass tags and are separated from one another, wherein the system is configured to (i) measure the abundance of the one or more mass tags at a plurality of locations occupied by the cells of the array using SIMS, (ii) generate a data set that comprises the measurements of the abundance of the one or more mass tags, and (iii) output the data set, and a computer comprising an analysis module that analyzes the data set.

The holder is in a movable stage that can be controllably moved (e.g., stepped or continuously moved) in at least the x and y directions (which are in the plane of the substrate) to facilitate scanning. The system may further contain an optical or electron imaging module to determine the location of the cells on the substrate, as described above. The analysis module can be programmed to perform many of the steps of the method described above. For example, in some embodiments, the analysis module may identify the locations of individual cells that are separated from one another based on a rapid survey scan, as described above, or identify subcellular features in individual cells, in the array of cells. In some cases, the analysis module may integrate the data for each of the individual cells or a subcellular feature thereof in the image and optionally categorize the individual cells based on the integrated data obtained for each of the cells. The analysis module may also display an image of the array, wherein the cells and/or subcellular features thereof are color-coded by their category. As noted above, in any one pixel of the image, the intensity of the color of the pixel correlates with the magnitude of the signals obtained for that pixel obtained by the SIMS system. In a particular embodiment, the system may comprise a DC ion source (i.e. dynamic source) linked to ion optics for focusing and filtering, then to an orthogonal ion pulser (pusher), then to a time of flight (TOF) tube for mass analysis and quantification. The SIMS system may be dynamic or static.

In some cases the present system may include a synchronizer that communicates between system components, such as a mass spectrometer, e.g., a TOF-MS, an ion beam source and/or a controller thereof, and/or a movable stage that holds the sample, where the synchronizer is configured to integrate mass detection events with the location on the sample upon which the ion beam impinges, and thereby to provide a spatial reference relative to the sample, e.g., location of the cell in the array, a site within a cell, or a subcellular structure of a cell, for the detected mass tags, as described above.

In certain embodiments, the analysis module may generate one or more histograms showing the abundance of the one or more mass tags associated with the cells, as described above. The histogram may be one, two, three dimensional or have a higher dimension. In certain embodiments, analysis module displays the location of each cell associated with a given level of abundance of one or more mass tags. In such a way, a user may be able to identify cells of interest on the substrate based on the measured level of abundance of one or more mass tags associated with the cells of interest. In certain embodiments, the system may include a laser microdissection module linked to the analysis module to facilitate recovery of the cells of interest.

In certain embodiments, the system is configured to generate a multiplexed data set comprising spatially-addressable measurements of the abundances of a plurality of mass tags that are bound to the cells. The analysis module may transform the plurality of mass tag measurements to produce a plurality of histograms. The analysis module may transform the plurality of mass tag measurements to produce a plurality images. Any convenient method may be used to generate and analyze images from the mass tag measurements, as described in, e.g., U.S. application Ser. No. 14/483,399, which is incorporated herein by reference.

The analysis method may be implemented on a computer. In certain embodiments, a general-purpose computer can be configured to a functional arrangement for the method and program disclosed herein. The hardware architecture of such a computer is well known by a person skilled in the art, and can comprise hardware components including one or more processors (CPU), a random-access memory (RAM), a read-only memory (ROM), an internal or external data storage medium (e.g., hard disk drive). A computer system can also comprise one or more graphic boards for processing and outputting graphical information to display means. The above components can be suitably interconnected via a bus inside the computer. The computer can further comprise suitable interfaces for communicating with general-purpose external components such as a monitor, keyboard, mouse, network, etc. In some embodiments, the computer can be capable of parallel processing or can be part of a network configured for parallel or distributive computing to increase the processing power for the present method and program. In some embodiments, the program code read out from the storage medium can be written into a memory provided in an expanded board inserted in the computer, or an expanded unit connected to the computer, and a CPU or the like provided in the expanded board or expanded unit can actually perform a part or all of the operations according to the instructions of the program code, so as to accomplish the functions described below. In other embodiments, the method can be performed using a cloud computing system. In these embodiments, the data files and the programming can be exported to a cloud computer, which runs the program, and returns an output to the user.

A system can in certain embodiments comprise a computer that includes: a) a central processing unit; b) a main non-volatile storage drive, which can include one or more hard drives, for storing software and data, where the storage drive is controlled by disk controller; c) a system memory, e.g., high speed random-access memory (RAM), for storing system control programs, data, and application programs, including programs and data loaded from non-volatile storage drive; d) system memory can also include read-only memory (ROM); a user interface, including one or more input or output devices, such as a mouse, a keypad, and a display; c) an optional network interface card for connecting to any wired or wireless communication network, e.g., a printer; and f) an internal bus for interconnecting the aforementioned elements of the system. The memory of a computer system can be any device that can store information for retrieval by a processor, and can include magnetic or optical devices, or solid state memory devices (such as volatile or non-volatile RAM). A memory or memory unit can have more than one physical memory device of the same or different types (for example, a memory can have multiple memory devices such as multiple drives, cards, or multiple solid state memory devices or some combination of the same). With respect to computer readable media, "permanent memory" refers to memory that is permanent. Permanent memory is not erased by termination of the electrical supply to a computer or processor. Computer hard-drive ROM (i.e., ROM not used as virtual memory), CD-ROM, floppy disk and DVD are all examples of permanent memory. Random Access Memory (RAM) is an example of non-permanent (i.e., volatile) memory. A file in permanent memory can be editable and re-writable.

Operation of computer is controlled primarily by operating system, which is executed by central processing unit. The operating system can be stored in a system memory. In some embodiments, the operating system can include a file system. In addition to an operating system, one possible implementation of the system memory includes a variety of programming files and data files for implementing the method described below. In certain cases, the programming can contain a program, where the program can be composed of various modules, and a user interface module that permits a user at user interface to manually select or change the inputs to or the parameters used by programming. The data files can include various inputs for the programming.

In certain embodiments, instructions in accordance with the method described herein can be coded onto a computer-readable medium in the form of "programming", where the term "computer readable medium" as used herein refers to any storage or transmission medium that participates in providing instructions and/or data to a computer for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer.

The computer-implemented method described herein can be executed using programming that can be written in one or more of any number of computer programming languages. Such languages include, for example, Java (Sun Microsystems, Inc., Santa Clara, CA), Visual Basic (Microsoft Corp., Redmond, WA), and C++ (AT&T Corp., Bedminster, NJ), as well as any many others.

Utility

The above-described method can be used to analyze a population of cells from a subject to determine, for example, whether the cells are normal or not or to determine whether the cells are responding to a treatment. In one embodiment, the method may be employed to determine the degree of dysplasia in cancer cells. In these embodiments, the cells may be from a sample of from a multicellular organism or a microbe. A biological sample may be isolated from an individual, e.g., from a soft tissue or from a bodily fluid, or from a cell culture that is grown in vitro. A biological sample may be made from a soft tissue such as brain, adrenal gland, skin, lung, spleen, kidney, liver, spleen, lymph node, bone marrow, bladder, stomach, small intestine, large intestine or muscle, etc. Bodily fluids include blood, plasma, saliva, mucous, phlegm, cerebral spinal fluid, pleural fluid, tears, lactal duct fluid, lymph, sputum, cerebrospinal fluid, synovial fluid, urine, amniotic fluid, and semen, etc. Biological samples also include cells grown in culture in vitro. A cell may be a cell of a tissue biopsy, scrape or lavage or cells.

The method described above finds particular utility in examining population of cells from body fluids or dissociated tissue using panels of antibodies. In some cases, blood cancer may be diagnosed based on detection of markers in a blood sample using the subject method. Exemplary blood cancer markers include: CD3, CD7, CD20, CD34, CD45, CD56, CD117, MPO, PAX-5, and TdT (acute leukemia); BCL-2, c-MYC, Ki-67 (Burkitt vs. DLBC lymphoma); BOB-1, BCL-6, CD3, CD10, CD15, CD20, CD30, CD45 LCA, CD79a, MUM1, OCT-2, PAX-5, and EBER ISH (Hodgkin vs. NHL); BCL-2, BCL-6, CD3, CD4, CD5, CD7, CD8, CD10, CD15, CD20, CD30, CD79a, CD138, cyclin D1, Ki67, MUM1, PAX-5, TdT, and EBER ISH (lymphoma); CD30, CD45, CD68, CD117, pan-keratin, MPO, S100, and synaptophysin (Lymphoma vs. Carcinoma); ALK1, CD2, CD3, CD4, CD5, CD7, CD8, CD10, CD20, CD21, CD30, CD56, TdT, and EBER ISH (T-Cell Lymphoma); BCL-2, BCL-6, CD3, CD5, CD10, CD20, CD23, CD43, cyclin D1, and Ki-67 (Lymphoma vs. Reactive Hyperplasia); and CD3, CD8, granzyme B, and TIA-1 (T-LGL Leukemia).

In some embodiments, the method may involve obtaining data as described above (an electronic form of which may have been forwarded from a remote location) and may be analyzed by a doctor or other medical professional to determine whether a patient has abnormal cells (e.g., cancerous cells) or which type of abnormal cells are present. The data may be used as a diagnostic to determine whether the subject has a disease or condition, e.g., a cancer. In certain embodiments, the method may be used to determine the stage of a cancer, to identify metastasized cells, or to monitor a patient's response to a treatment, for example.

In any embodiment, data can be forwarded to a "remote location", where "remote location," means a location other than the location at which the data is examined. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or at least one hundred miles apart. "Communicating" information references transmitting the data representing that information as electrical signals over a suitable communication channel (e.g., a private or public network). "Forwarding" an item refers to any means of getting that item from one location to the next, whether by physically transporting that item or otherwise (where that is possible) and includes, at least in the case of data, physically transporting a medium carrying the data or communicating the data. Examples of communicating media include radio or infra-red transmission channels as well as a network connection to another computer or networked device, and the internet or including email transmissions and information recorded on websites and the like. In certain embodiments, the data may be analyzed by an MD or other qualified medical professional, and a report based on the results of the analysis of the data may be forwarded to the patient from which the sample was obtained.

In certain cases, the portions of the cells remaining on the substrate after being analyzed by SIMS may be recovered selectively to further analyze cells of interest, as described above. Exemplary analyses that may be performed on the recovered cells include sequencing (e.g., next generation sequencing) of nucleic acids, proteomic and metabolomics analyses, fluorescence imaging, Raman spectroscopy, nuclear magnetic resonance, etc. The further analysis may be used to confirm the results of the SIMS analysis, to obtain genomic, proteomic, etc., information, or to otherwise further characterize the biological properties of the cells of interest recovered based on the SIMS analysis.

In some cases, the method may be employed in a variety of diagnostic, drug discovery, and research applications that include, but are not limited to, diagnosis or monitoring of a disease or condition (where the abundance and/or localization of one or more mass tags identifies a marker for the disease or condition), discovery of drug targets (where the a marker associated with cells in the data may be targeted for drug therapy), drug screening (where the effects of a drug are monitored by the abundance and/or localization of one or more mass tags), determining drug susceptibility (where drug susceptibility is associated with a marker) and basic research (where is it desirable to measure the differences between cells in a sample).

In certain embodiments, two different samples may be compared using the above method. The different samples may be composed of an "experimental" sample, i.e., a sample of interest, and a "control" sample to which the experimental sample may be compared. In many embodiments, the different samples are pairs of cell types or fractions thereof, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell may be compared. Exemplary cell type pairs include, for example, cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be employed. In another embodiment of the invention, the experimental material is cells susceptible to infection by a pathogen such as a virus, e.g., human immunodeficiency virus (HIV), etc., and the control material is cells resistant to infection by the pathogen. In another embodiment, the sample pair is represented by undifferentiated cells, e.g., stem cells, and differentiated cells.

Cells from any organism, e.g., from bacteria, yeast, plants and animals, such as fish, birds, reptiles, amphibians and mammals may be used in the subject method. In certain embodiments, mammalian cells, i.e., cells from mice, rabbits, primates, or humans, or cultured derivatives thereof, may be used.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Example 1: Single Cell Mass Tomography from SIMS Analysis of Arrayed Cells

In implementing the present method, the inherent curvature of the cell may distort the SIMS primary ion beam analysis plane as it burrows through the cell across repeat scans (FIG. 3, top). Predictable, cell compartment specific mass reporter signatures are attainable by modeling the curved plane and applying cell localization standards (FIG. 3, bottom).

Example 2: SIMS Depth Profile of a Single Cell Reveals Relative Sub-Cellular Localization of Expressed Components FIG. 4 shows a low resolution (>1 µm beam size) sequential scan of an immobilized human Jurkat T cell stained with mono isotopic elemental reporters for the surface molecule CD3 and CD45, cytosolic molecule ribosomal protein S6, and nuclear molecule double stranded DNA (sDNA). As each layer of the immobilized cell was ablated and analyzed by the oxygen duoplasmatron beam the normalized expression (Y axis) of the aforementioned molecules changed in a pattern corresponding to their expected localization. First, CD3 and CD45 were at maximal expression, then as the analysis depth into the cell increased (increased plan number—X axis) S6 reached a maximum followed by dsDNA. Visual correlation with the differential expression patterns at the indicated SIMS depth planes were observed, as shown in the inset images.

Example 3: Correlation Analysis Reveals Localization

Plotting known reporter signals for cell localization analysis on a scan-by-scan basis revealed co-localization. As shown in FIG. 5, the NFKB negative regulator IkB alpha was co-localized with cytosolic actin (black arrow).

What is claimed is:

1. A method of analyzing a population of cells, comprising:
   i) providing multiple individual cells on a substrate, wherein each cell is labeled with one or more mass tags and does not contact other cells on the substrate;
   ii) measuring, by scanning the individual cells on the substrate with an ionizing beam that generates ions from the cells, an abundance of the one or more mass tags for the individual cells and generating a set of data comprising, for each of the individual cells, mass tag abundance measurements at multiple locations within the individual cells; and
   iii) outputting the set of data.

2. The method of claim 1, wherein the individual cells are arranged in an array that comprises a regular arrangement of addressable locations.

3. The method of claim 1, wherein the individual cells are arranged in an array that comprises a non-regular arrangement of locations and the locations occupied by the cells are determined by imaging the substrate prior to the measuring step.

4. The method of claim 3, wherein the imaging is by optical imaging, electron imaging or secondary ion mass spectrometry.

5. The method of claim 1, wherein step ii) comprises exposing the individual cells to a plurality of pulses of the ionizing beam at different locations in the cell to obtain the mass tag abundance measurements at the multiple locations within the individual cells.

6. The method of claim 5, wherein the ionizing beam has a diameter in the range of 10 nm to 1500 nm.

7. The method of claim 6, wherein the method comprises measuring the abundances of the one or more mass tags at a plurality of depths within one or more of the individual cells as the ionizing beam etches through the one or more of the individual cells.

8. The method of claim 1, wherein:
   labeling the individual cells with the one or more mass tags; and
   attaching the individual cells to the substrate,
   wherein the labeling is performed either prior to or after the individual cells are attached to the substrate.

9. The method of claim 8, wherein the labeling is performed by administering the one or more mass tags to an animal subject and obtaining labeled cells from the subject.

10. The method of claim 1, wherein each cell is labeled with at least a first mass tag that localizes to a known subcellular structure of the cell and a second mass tag, and wherein the method comprises:
   measuring the abundances of the first and second mass tags at different locations within the individual cells; and
   determining subcellular localization of the second mass tag based on the measured abundances of the first and second mass tags.

11. The method of claim 1, further comprising:
   iv) identifying one or more individual cells of interest based on the set of data; and
   v) recovering the identified cells of interest from the substrate for further analysis.

12. A method of analyzing a test population of cells, comprising:
   i) providing multiple individual cells of the test population on a substrate, wherein each cell is labeled with one or more mass tags;
   ii) measuring, by scanning the individual cells on the substrate with an ionizing beam that generates ions from the cells, an abundance of the one or more mass tags for the individual cells and generating a set of data comprising, for each of the individual cells, mass tag abundance measurements;
   iii) for each of the individual cells, comparing the set of data expressible as a histogram to reference information expressible as a reference histogram obtained from a reference population of cells to identify one or more cells of interest among the individual cells; and
   iv) selectively removing the one or more cells of interest from the substrate.

13. The method of claim 12, wherein comprising identifying the one or more cells of interest based on one or more threshold values for the abundances of the one or more mass tags.

14. The method of claim 13, comprising determining the one or more threshold values from the reference information expressible as a reference histogram.

15. The method of claim 12, wherein providing the multiple individual cells on the substrate comprises contacting the multiple individual cells with a test agent to which the reference population of cells is not contacted.

16. The method of claim 12, comprising obtaining the test population of cells from a subject diagnosed with a condition, wherein the reference population of cells corresponds to normal cells.

17. A system for analyzing individual cells, the system comprising:
   a holder for retaining a substrate comprising multiple individual cells, wherein the individual cells are labeled with one or more mass tags and do not contact other cells on the substrate;
   a source of an ionizing beam that generates ions from the individual cells;
   an ion detector;
   a cell recovery apparatus; and
   a computational device,
   wherein the system is programmed to:
      (i) measure abundances of the one or more mass tags for the individual cells;
      (ii) generate a data set comprising, for each of the individual cells, mass tag abundance measurements;
      (iii) identify, based on the data set, one or more cells of interest among the individual cells; and
      (iv) selectively remove the one or more cells of interest from the substrate.

18. The system of claim 17, wherein the cell recovery apparatus comprises a micropipette.

19. The system of claim 17, wherein the cell recovery apparatus comprises a laser microdissection module.

\* \* \* \* \*